US011708337B2

(12) United States Patent
Schneider et al.

(10) Patent No.: US 11,708,337 B2
(45) Date of Patent: Jul. 25, 2023

(54) SYNTHESIS OF 1,4-DIAZASPIRO[5.5]UNDECAN-3-ONE

(71) Applicant: G1 Therapeutics, Inc., Research Triangle Park, NC (US)

(72) Inventors: Stephen E. Schneider, Raleigh, NC (US); Hannah White, Chapel Hill, NC (US); Thomas Fessard, Basel (CH); Sagar Beldar, Basel (CH)

(73) Assignee: G1 Therapeutics, Inc., Research Triangle Park, NC (US)

( * ) Notice: Subject to any disclaimer, the term of this patent is extended or adjusted under 35 U.S.C. 154(b) by 0 days.

(21) Appl. No.: 17/184,354

(22) Filed: Feb. 24, 2021

(65) Prior Publication Data
US 2021/0179567 A1    Jun. 17, 2021

Related U.S. Application Data

(63) Continuation of application No. PCT/US2019/048029, filed on Aug. 23, 2019.

(60) Provisional application No. 62/722,675, filed on Aug. 24, 2018.

(51) Int. Cl.
*C07C 219/18* (2006.01)
*C07D 241/38* (2006.01)
*C07D 239/47* (2006.01)

(52) U.S. Cl.
CPC .......... *C07D 241/38* (2013.01); *C07C 219/18* (2013.01); *C07D 239/47* (2013.01)

(58) Field of Classification Search
CPC .. C07C 219/18; C07D 239/47; C07D 241/38; C07D 487/14; C07D 487/20
See application file for complete search history.

(56) References Cited

U.S. PATENT DOCUMENTS

| | | | |
|---|---|---|---|
| 6,506,760 B1 | 1/2003 | Araldi et al. | |
| 6,962,993 B2 | 11/2005 | Blumenkopf et al. | |
| 7,345,171 B2 | 3/2008 | Beylin et al. | |
| 10,202,392 B2 | 2/2019 | Tavares | |
| 2004/0236084 A1 | 11/2004 | Biwersi et al. | |
| 2005/0154000 A1 | 7/2005 | Jolidon et al. | |
| 2006/0142312 A1 | 6/2006 | Flamme et al. | |
| 2009/0264401 A1 | 10/2009 | Gill et al. | |
| 2011/0009353 A1 | 1/2011 | Chen-Kiang et al. | |
| 2011/0312909 A1 | 12/2011 | Ciomei et al. | |
| 2014/0271466 A1 | 9/2014 | Sharpless et al. | |
| 2015/0031674 A1 | 1/2015 | Rudolph et al. | |
| 2015/0297608 A1 | 10/2015 | Strum et al. | |
| 2016/0108054 A1 | 4/2016 | Tavares et al. | |
| 2018/0208608 A1 | 7/2018 | Brodney et al. | |

FOREIGN PATENT DOCUMENTS

| | | |
|---|---|---|
| CN | 105622638 A | 6/2016 |
| WO | WO 1998/033798 A2 | 8/1998 |
| WO | WO 1999/015500 A1 | 4/1999 |
| WO | WO 2002/01223 8 A2 | 2/2002 |
| WO | WO 2003/06223 6 A1 | 7/2003 |
| WO | WO 2004/047725 A2 | 6/2004 |
| WO | WO 2005/005426 | 1/2005 |
| WO | WO 2005/040166 A1 | 5/2005 |
| WO | WO 2005/052147 A2 | 6/2005 |
| WO | WO 2005/105213 A2 | 11/2005 |
| WO | WO 2006/029153 A2 | 3/2006 |
| WO | WO 2006/031606 A2 | 3/2006 |
| WO | WO 2006/031610 A2 | 3/2006 |
| WO | WO 2006/074985 A1 | 7/2006 |
| WO | WO 2007/048847 A2 | 5/2007 |
| WO | WO 2007/061677 A2 | 5/2007 |
| WO | WO 2008/073251 A1 | 6/2008 |
| WO | WO 2008/109464 A1 | 9/2008 |
| WO | WO 2009/003 003 A2 | 12/2008 |
| WO | WO 2009/085185 A1 | 7/2009 |
| WO | WO 2010/020675 A1 | 2/2010 |
| WO | WO 2010/03 9997 A2 | 4/2010 |
| WO | WO 2010/051127 A2 | 5/2010 |
| WO | WO 2010/132725 A2 | 11/2010 |
| WO | WO 2011/101409 A1 | 8/2011 |
| WO | WO 2011/103485 A1 | 8/2011 |
| WO | WO 2012/061156 A1 | 5/2012 |
| WO | WO 2013/148748 A1 | 10/2013 |
| WO | WO 2013/163239 A1 | 10/2013 |
| WO | WO 2013/169574 A2 | 11/2013 |
| WO | WO 2014/168975 A1 | 10/2014 |
| WO | WO 2015/061407 A1 | 4/2015 |
| WO | WO 2018/005865 * | 1/2018 |
| WO | WO 2018/005865 A1 | 1/2018 |

OTHER PUBLICATIONS

Ono, The Nitro Group in Organic Synthesis, Chapter 3, pp. 30-69, (2001).*

(Continued)

*Primary Examiner* — Deepak R Rao
(74) *Attorney, Agent, or Firm* — Knowles Intellectual Property Strategies, LLC

(57) ABSTRACT

This invention provides a process for preparing 1,4-diazaspiro[5.5]undecan-3-one and analogues thereof that are useful in the preparation of pharmaceutical compound, including for the treatment of disorders involving abnormal cellular proliferation. Chemical intermediates in the process are also provided.

26 Claims, 1 Drawing Sheet

(56) References Cited

OTHER PUBLICATIONS

U.S. Pat. No. 8,598,186, B2, U.S. Appl. No. 13/869,520, Tavares et al., Dec. 3, 2013.
U.S. Pat. No. 8,598,197, B2, U.S. Appl. No. 13/869,576, Tavares et al., Dec. 3, 2013.
U.S. Pat. No. 8,691,830, B2, U.S. Appl. No. 13/869,594, Tavares et al., Apr. 8, 2014.
U.S. Pat. No. 8,822,683, B2, U.S. Appl. No. 14/162,637, Tavares et al., Sep. 2, 2014.
U.S. Pat. No. 8,829,012, B2, U.S. Appl. No. 14/162,649, Tavares et al., Sep. 9, 2014.
U.S. Pat. No. 9,102,682, B2, U.S. Appl. No. 14/452,296, Tavares et al., Aug. 11, 2015.
U.S. Pat. No. 9,260,442, B2, U.S. Appl. No. 14/498,796, Tavares, Jan. 27, 2016.
U.S. Pat. No. 9,464,092, B2, U.S. Appl. No. 14/212,911, Strum et al., Oct. 11, 2016.
U.S. Pat. No. 9,481,691, B2, U.S. Appl. No. 14/712,630, Tavares et al., Nov. 1, 2016.
U.S. Pat. No. 9,487,530, B2, U.S. Appl. No. 14/212,430, Strum et al., Nov. 8, 2016.
U.S. Pat. No. 9,499,564, B2, U.S. Appl. No. 14/712,582, Tavares et al., Nov. 22, 2016.
U.S. Pat. No. 9,527,857, B2, U.S. Appl. No. 14/214,048, Strum et al., Dec. 27, 2016.
U.S. Pat. No. 9,717,735, B2, U.S. Appl. No. 14/690,180, Strum et al., Aug. 1, 2017.
U.S. Pat. No. 9,745,316, B2, U.S. Appl. No. 14/982,443, Tavares, Aug. 29, 2017.
U.S. Pat. No. 9,856,268, B2, U.S. Appl. No. 15/348,862, Tavares, Jan. 2, 2018.
U.S. Pat. No. 9,931,345, B2, U.S. Appl. No. 15/288,878, Strum et al., Apr. 3, 2018.
U.S. Pat. No. 9,957,276, B2, U.S. Appl. No. 15/348,770, Tavares, et al., May 1, 2018.
U.S. Pat. No. 10,076,523, B2, U.S. Appl. No. 15/387,083, Strum et al., Sep. 18, 2018.
U.S. Pat. No. 10,085,992, B2, U.S. Appl. No. 15/342,990, Strum et al., Oct. 2, 2018.
U.S. Pat. No. 10,189,849, B2, U.S. Appl. No. 15/918,834, Tavares et al., Jan. 29, 2019.
U.S. Pat. No. 10,189,850, B2, U.S. Appl. No. 15/918,852, Tavares et al., Jan. 29, 2019.
U.S. Pat. No. 10,189,851, B2, U.S. Appl. No. 15/918,877, Tavares et al., Jan. 29, 2019.
U.S. Pat. No. 10,231,969, B2, U.S. Appl. No. 15/457,699, Strum, et al., Mar. 19, 2019.
U.S. Pat. No. 10,376,519, B2, U.S. Appl. No. 15/665,071, Strum, et al., Aug. 13, 2019.
U.S. Pat. No. 10,413,547, B2, U.S. Appl. No. 16/142,574, Strum, et al., Sep. 17, 2019.
U.S. Pat. No. 10,434,104, B2, U.S. Appl. No. 16/112,362, Strum, et al., Oct. 8, 2019.
U.S. Pat. No. 10,464,940, B2, U.S. Appl. No. 15/860,483, Tavares et al., Nov. 5, 2019.
U.S. Pat. No. 10,618,905, B2, U.S. Appl. No. 16/230,412, Strum, et al., Apr. 14, 2020.
U.S. Pat. No. 10,660,896, B2, U.S. Appl. No. 15/943,278, Strum, et al., May 26, 2020.
U.S. Pat. No. 10,654,831, B2, U.S. Appl. No. 16/230,388, Strum, et al., May 19, 2020.
U.S. Pat. No. 10,696,682, B2, U.S. Appl. No. 16/226,430, Tavares et al., Jun. 30, 2020.
U.S. Pat. No. 10,709,711, B2, U.S. Appl. No. 16/228,308, Strum et al., Jul. 14, 2020.
U.S. Pat. No. 10,829,490, B2, U.S. Appl. No. 16/230,396, Strum et al., Nov. 10, 2020.
U.S. Pat. No. 10,865,210, B2, U.S. Appl. No. 16/230,381, Smith et al., Dec. 15, 2020.
U.S. Pat. No. 10,925,878, B2, U.S. Appl. No. 16/178,419, Strum et al., Feb. 23, 2021.
U.S. Pat. No. 10,927,120, B2, U.S. Appl. No. 16/721,631, Smith et al., Feb. 23, 2021.
U.S. Pat. No. 10,966,984, B2, U.S. Appl. No. 16/112,360, Strum et al., Apr. 6, 2021.
U.S. Pat. No. 10,981,887, B2, U.S. Appl. No. 16/824,290, Strum et al., Apr. 20, 2021.
U.S. Pat. No. 10,988,479, B2, U.S. Appl. No. 17/097,854, Schneider, Apr. 27, 2021.
U.S. Pat. No. 11,040,042, B2, U.S. Appl. No. 16/886,309, Strum et al., Jun. 22, 2021.
U.S. Pat. No. 11,090,306, B2, U.S. Appl. No. 16/572,418, Strum, et al., Aug. 17, 2021.
U.S. Pat. No. 11,261,193, B2, U.S. Appl. No. 16/721,631, Smith et al., Mar. 1, 2022.
U.S. Pat. No. 11,357,779, B2, U.S. Appl. No. 16/924,033, Beelen et al., Jun. 14, 2022.
U.S. Pat. No. 11,395,821, B2, U.S. Appl. No. 16/547,342, Sorrentino, et al., Jul. 26, 2022.
U.S. Pat. No. 11,446,295, B2, U.S. Appl. No. 16/254,364, Strum, et al., Sep. 20, 2022.
2019/0167691 A1, U.S. Appl. No. 16/268,317 Strum, et al. Jun. 6, 2019.
2019/0321370 A1, U.S. Appl. No.16/432,244, Sorrentino, et al., Oct. 24, 2019.
2020/0283406 A1 U.S. Appl. No. 16/877,249, Strum, et al., Sep. 10, 2020.
2020/0345743 A1, U.S. Appl. No. 16/926,035, Strum, et al., Nov. 5, 2020.
2021/0030758 A1, U.S. Appl. No. 17/067,549 Strum, et al., Feb. 4, 2021.
2021/0077498 A1, U.S. Appl. No. 17/102,311, Strum, et al., Mar. 18, 2021.
2021/0122755, A1, U.S. Appl. No.17/121,392, Smith et al., Apr. 29, 2021.
2021/0213022, A1, U.S. Appl. No. 17/181,638, Strum, et al., Jul. 15, 2021.
2021/0179567, A1, U.S. Appl. No. 17/184,354, Schneider et al., Jun. 17, 2021.
2021/0267986, A1, U.S. Appl. No.17/315,011, Sorrentino et al., Sep. 2, 2021.
2021/0387993, A1, U.S. Appl. No. 17/236,687, Schneider et al., Dec. 16, 2021.
2021/0299130, A1, U.S. Appl. No. 17/222,873, Strum, et al., Sep. 30, 2021.
2022/0175780, A1, U.S. Appl. No. 17/403,577, Strum, et al., Jun. 9, 2022.
2022/0175787, A1 U.S. Appl. No. 17/554,940, Roberts et al., Jun. 9, 2022.
2022/0241275, A1, U.S. Appl. No. 17/718,052, Strum et al., Aug. 4, 2022.
U.S. Appl. No. 17/683,146, Smith et al., filed Feb. 28, 2022.
U.S. Appl. No. 17/890,130, Strum et al., filed Aug. 17, 2022.
U.S. Appl. No. 17/854,755, Sorrentino et al., filed Jun. 30, 2022.
U.S. Appl. No. 17/839,215, Beelen et al., filed Jun. 13, 2022.
U.S. Appl. No. 17/898,196, Strum et al., filed Aug. 29, 2022.
Beadle, Jonathan et al. Synthesis of Oxetane- and Azetidine-Containing Spirocycles Related to the 2, 5-Diketopiperazine Framework, Synlett, vol. 27, No. 1, Dec. 17, 2015; pp. 169-172.
Chu et al. "Discovery of [4-Amino-2-(1-methanesulfonylpiperidin-4-ylamino)pyrimidin-5-yl](2,3-difluoro-6-methoxyphenyl)methanone (R547), a potent and selective cyclin-dependent kinase inhibitor with significant in vivo antitumor activity" J Med Chem, Nov. 2, 2006; 49(22): 6549-6560.
Duan et al., "Palbociclib Commercial Manufacturing Process Development. Part 1: Control of Regioselectivity in a Grignard-Mediated SnAr Coupling" OPR&D, DOI:10.1021/acs.oprd.6b00070.
Eary et al., "Tetrazole and ester substituted tetrahydroquinoxalines as potent cholesteryl ester transfer protein inhibitors," Bioorganic & Medicinal Chemistry Letters, 2007, vol. 17, pp. 2608-2613.

(56) References Cited

OTHER PUBLICATIONS

Fabris, et al. Methyl carbonate and Bicarbonate Phosphonium Salts as Catalysts for the Nitroaldol (Henry) Reaction in Journal of Organic Chemistry, 2012, vol. 77, pp. 1805-1811.

Goldberg et al. "Pyrazinoindolone inhibitors of MAPKAP-K2" Bioogranic & Medicinal Chemistry Letters, Dec. 23, 2007, 18, 938-941.

Griffith et al., "Spirolactam-Based Acetyl-CoA Carboxylase Inhibitors: Toward Improved Metabolic Stability of a Chromanone Lead Structure" Journal of Medicinal Chemistry 56(17): 7110-7119; 2013.

Guillard et al., "Synthesis and biological evaluations of new pyrrolo[2,3-b]pyrimidine as SDI analogs" Heterocyles, 2008, vol. 75(5), pp. 1163-1189.

International search report and written opinion for PCT/US2019/048029 dated Nov. 19, 2019.

Kotsuki et al., "An Efficient Procedure for Palladium Catalyzed Reduction of Aryl/Enoi Triflates," Synthesis 1995, vol. 11, pp. 1348-1350.

Kubinyi (3D QSAR in Drug Design: Ligand-Protein Interactions and Molecular Similarity, vol. 2-3, Springer, 1998, 800 pages). p. 243-44.

McInnes, C. "Progress in the evaluation of CDK inhibitors as anti-tumor agents" DrugDiscov Today, Oct. 2008; 13(19-20): 875-881.

Ono, N. "The Nitro-Aldol (Henry) Reaction," The Nitro Group in Organic Synthesis, 2001, pp. 30-69, p. 31, Scheme 3. 1; p. 34, Table 3. 1; p. 35.

Park et al. "Toxixogenetics in drug development" Toxicology Letters, Mar. 31, 2001, 120, 281-291.

Presser, Armin and Antje Hüfner "Trimethylsilyldiazomethane—A Mild and Efficient Reagent for the Methylation of Carboxylic Acids and Alcohols in Natural Products" Monatshefte für Chemie, 2004, vol. 135, Issue 8, pp. 1015-1022.

Rajak, H. et al., "2,5-Disubstituted-1,3,4-oxadiazoles/thiadiazole as surface recognition moiety: Design and synthesis of novel hydroxamic acid-based histone deacetylase inhibitors", Bioorganic & Medicinal Chemistry Letters, Pergamon, Amsterdam, NL, vol. 21, No. 19, Aug. 3, 2011.

Reddy, M.V.R. et al., Discovery of 8-Cyclopentyl-2-[4-(4-methyl-piperazin-1-yl)-phenylamino]-7-oxo—7,8-dihydro-pyrido[2,3-d]pyrimidine-6-carbonitrile (7x) as a Potent Inhibitor of Cyclin-Dependent Kinase 4 (CDK4) and AMPK-Related Kinase 5 (ARK5), J. Med. Chem., 2014, vol. 57, op. 578-599.

Schönauer, K. and E. Zibral "Reactions with organophosphorus compounds, 50.: Trimethylsilylethoxymethylene triphenylphosphorane, a novel reagent for the homologation of carbonyl compounds." Tetrahedron Letters, 1983; 24: 573-576.

Shimamura, T. et al. "Identification of potent 5-pyrimidinyl-2-aminothiazole CDK4, 6 inhibitors with significant selectivity over CDK1, 2, 5, 7, and 9" Bioorg Med Chem Lett., Jul. 15, 2006; 16(14): 3751-3754.

Sielecki et al. (BMCL 11 (2001) 1157-1160).

Soni, R. et al. "Selective in vivo and in vitro effects of a small molecule inhibitor of cyclin-dependent kinase 4" J Natl Cancer Inst, Mar. 21, 2001; 93(6): 436-446.

Toogood, P. L. et al. "Discovery of a potent and selective inhibitor of cyclin-dependent kinase 4/6" J Med Chem, Apr. 7, 2005; 48(7): 2388-2406.

Wermuth, The Practice of Medicinal Chemistry, 2d ed. (2003), 768 pages. Chs. 9-10.

White, J.D et al. "Transformations of Quinic Acid. Asymmetric Synthesis and Absolute Configuration of Mycosporin I and Mycosporin-gly" Journal of Organic Chemistry, 1995, vol. 60, Issue 12, pp. 3600-3611.

* cited by examiner

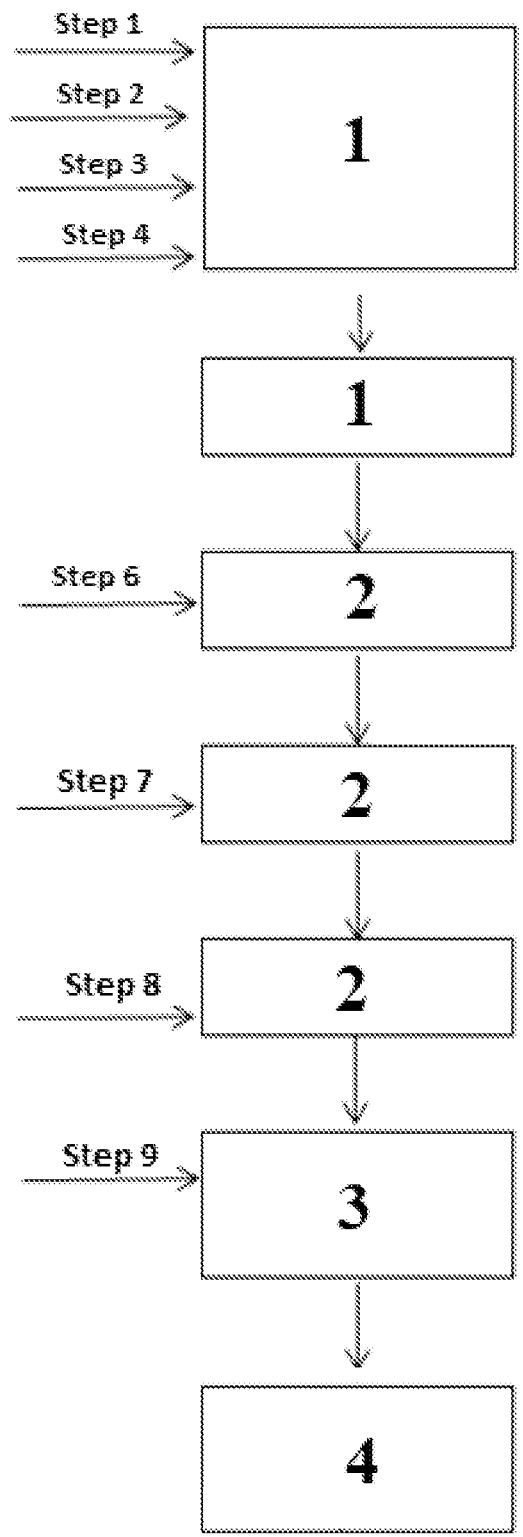

SYNTHESIS OF 1,4-DIAZASPIRO[5.5]UNDECAN-3-ONE

RELATED APPLICATIONS

This application continuation of International Patent Application No. PCT/US2019/048029, filed in the U.S. Receiving Office on Aug. 23, 2019, which claims the benefit of provisional U.S. Application No. 62/722,675, filed Aug. 24, 2018. The entirety of each these applications is hereby incorporated by reference herein for all purposes.

FIELD OF THE INVENTION

This invention provides a process for preparing 1,4-diazaspiro[5.5]undecan-3-one and analogues thereof that are useful in the preparation of certain pharmaceutical compounds, including for the treatment of disorders involving abnormal cellular proliferation. Chemical intermediates in the process are also provided.

BACKGROUND

U.S. Pat. Nos. 8,822,683; 8,598,197; 8,598,186; 8,691,830; 8,829,102; 8,822,683; 9,102,682; 9,499,564; 9,481,591; and U.S. Pat. No. 9,260,442; filed by Tavares and Strum and assigned to G1 Therapeutics describe compounds that include a spirocyclic core. Specifically, these patents describe a class of N-(heteroaryl)-pyrrolo[3,2-d]pyrimidin-2-amine cyclin dependent kinase inhibitors including those of the formula (with variables as defined therein):

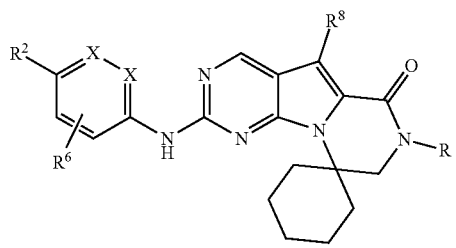

U.S. Pat. Nos. 9,464,092; 9,487,530; and 9,527,857 which are also assigned to G1 Therapeutics describe the use of such compounds to treat cancer.

The patents cited above use a multistep process in which the spirocycle core is formed late in the process by intramolecular cyclization. The process starts with commercially available tert-butyl (1-(aminomethyl)cyclohexyl)carbamate and uses several protecting and deprotecting steps to control the selectivity of the two amino groups throughout the synthesis. After cyclization the desired heteroaryl group is added by a nucleophilic aromatic substitution reaction. This process is shown in Scheme 1 below.

Scheme 1.
Prior synthesis of N-(heteroaryl)-pyrrolo[3,2-d]pyrimidin-2-amine cyclin dependent kinase inhibitors.

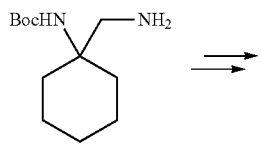

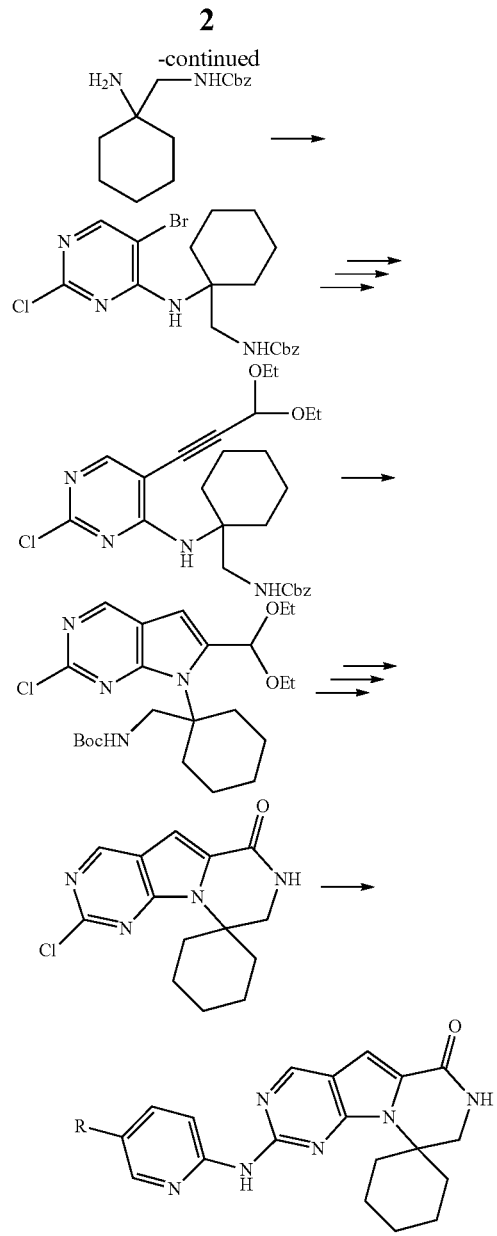

Another process to synthesize N-(heteroaryl)-pyrrolo[3,2-d]pyrimidin-2-amine cyclin dependent kinase inhibitors was disclosed in PCT Application WO 2018/005865. This process provided several improvements over prior methods including the use of 1,4-diazaspiro[5.5]undecan-3-one as an intermediate.

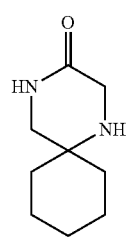

1,4-diazaspiro[5.5]undecan-3-one

The '865 application also provides a process to synthesize 1,4-diazaspiro[5.5]undecane-3-one. This process affords 1,4-diazaspiro[5.5]undecane-3-one in six steps from commercially available cyclohexanone This process is summarized below in Scheme 2.

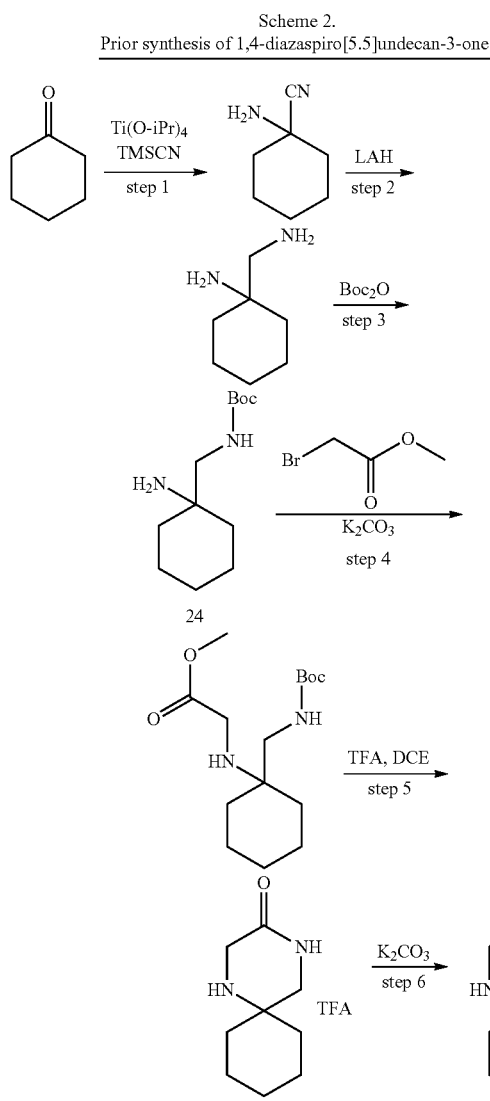

There remains a need for processes that have higher yields, require fewer and/or milder chemical reactions, and/or have fewer steps to synthesize 1,4-diazaspiro[5.5]undecan-3-one.

SUMMARY OF THE INVENTION

It has been discovered that 1,4-diazaspiro[5.5]undecan-3-one and structural analogues (Formula II and Formula IV below) can be advantageously prepared in a two-pot process from cyclohexanone. In the first pot, cyclohexenone is reacted with nitromethane to produce 1-(nitromethyl)cyclohexan-1-ol, which then loses water to produce (nitromethylene)cyclohexane. An alkyl glycinate is then added to (nitromethylene)cyclohexane to produce alkyl (1-(nitromethyl)cyclohexyl)glycinate. Then in the second pot, the nitro group of (1-(nitromethyl)cyclohexyl)glycinate is converted to an amino group to produce methyl (1-(aminomethyl)cyclohexyl)glycinate. The alkyl group is then removed to produce (1-(aminomethyl)cyclohexyl)glycine. This compound then internally cyclizes to produce 1,4-diazaspiro[5.5]undecan-3-one. In one embodiment, the cyclization occurs in the absence of hydrolysis. This synthetic sequence is shown below in Scheme 3.

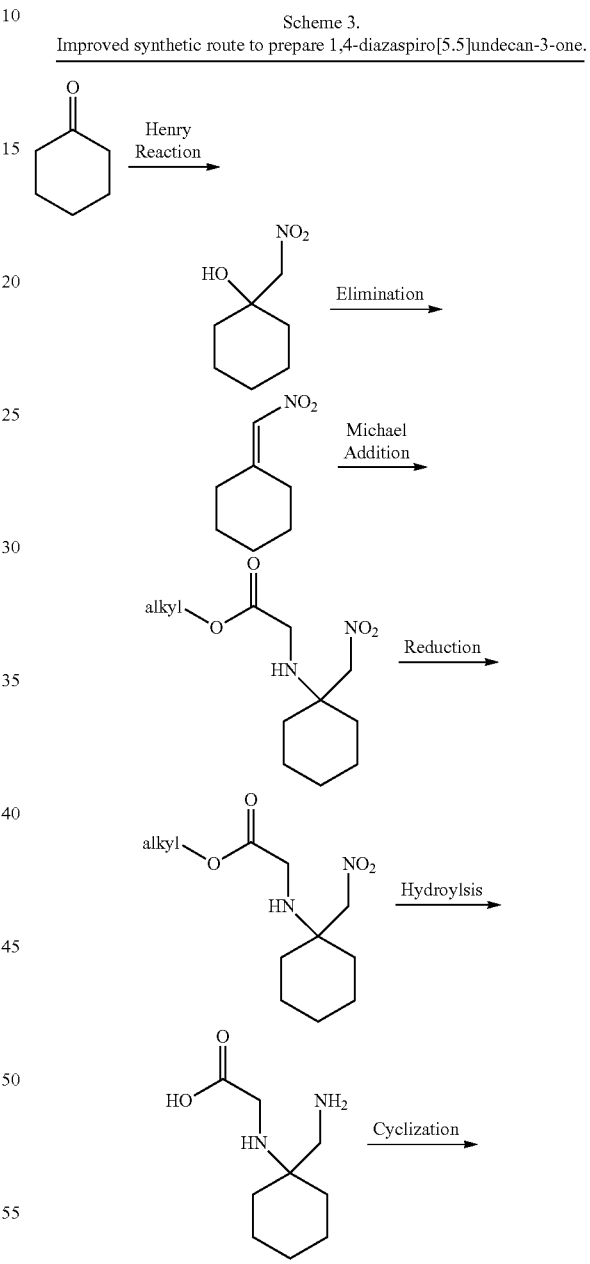

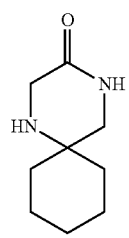

Advantageously, in one aspect of the present invention, one or more of the mechanistic steps shown in Scheme 3 may be conducted in the same reaction vessel without isolation. For example, the Henry reaction, elimination, and Michael addition can all be combined in one reaction. Similarly, the reduction, hydrolysis and cyclization reaction can also be combined in one reaction. An example of this advantageous embodiment is presented in Scheme 4 below.

Scheme 4.
Preparation of 1,4-diazaspiro[5.5]
undecan-3-one with only two isolations.

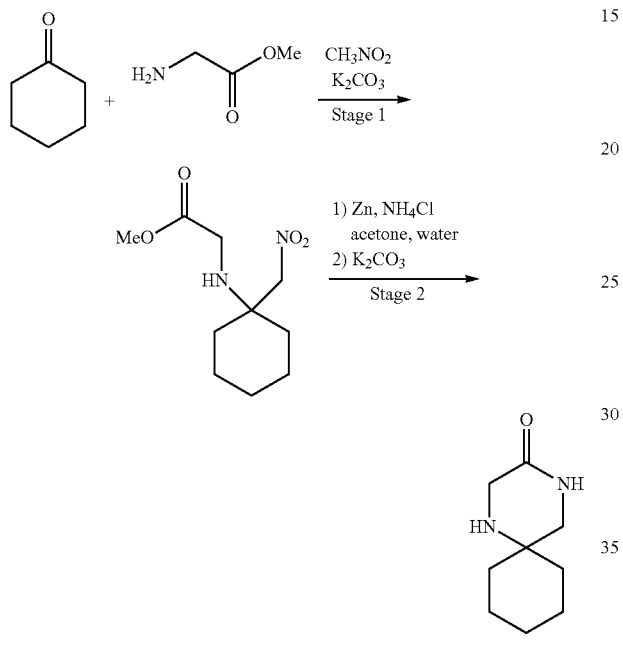

In another aspect of the present invention, one or more of the isolation steps can be accomplished by recrystallization or filtration after addition of an acid. For example, in Scheme 5 below, a hydrobromic acid workup allowed for high yield isolation of the Michael adduct by filtration.

Scheme 5.
Utilization of hydrobromic acid to
isolate the Michael addition product.

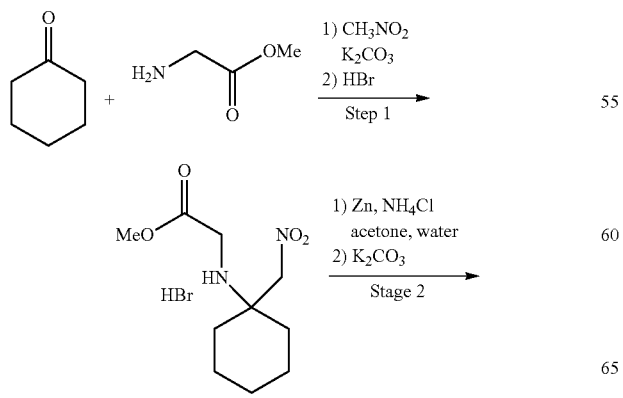

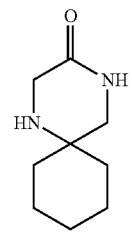

As described in more detail in the detailed description below, having been taught this reaction, the skilled worker can select alternative reagents, reactants, and solvents other than those presented in Scheme 4 and Scheme 5 to achieve a desired similar result. For example, Scheme 6 provides a more generalized version of the reaction which still uses only two isolation steps.

Scheme 6.
General preparation of 1,4-diazaspiro[5.5]
undecan-3-one with only two isolations.

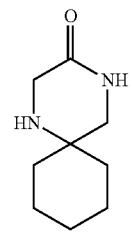

In another aspect of the invention, the methods described herein can be used to produce compounds of Formula II.

Scheme 7.
General preparation of 1,4-diazaspiro[5.5]
undecan-3-one with only two isolation steps.

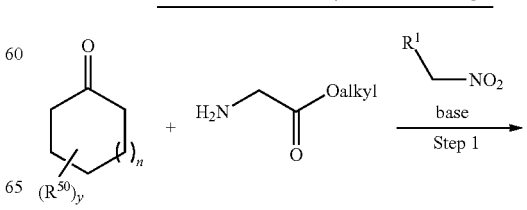

7
-continued

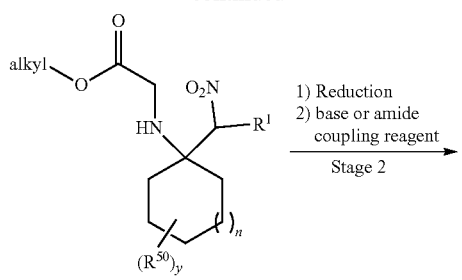

Formula I

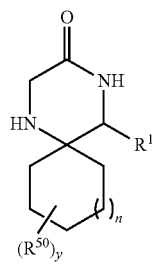

Formula II

Wherein:
y is 0, 1, 2, 3, or 4;
n is 0 or 1;
R¹ is selected from hydrogen, alkyl, and aryl; and
each instance of R⁵⁰ is independently selected from hydrogen, halogen, and alkyl.

In another aspect of the invention, the methods described herein can be used to produce compounds of Formula IV.

Scheme 8.
General preparation of compounds
of Formula IV with only two isolation steps.

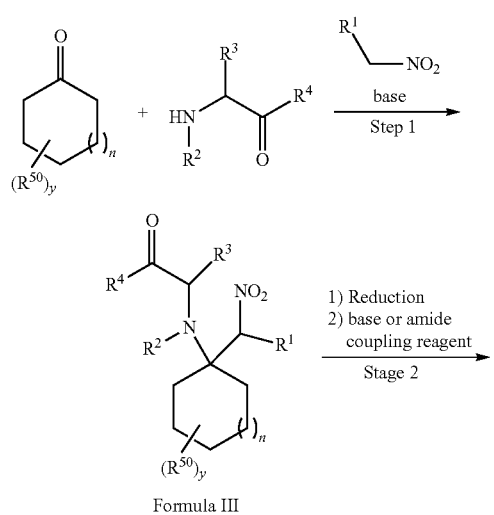

Formula III

8
-continued

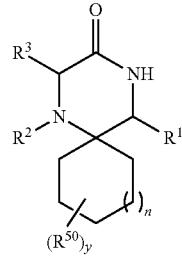

Formula IV wherein:
y is 0, 1, 2, 3, or 4;
n is 0 or 1;
R¹ is selected from hydrogen, alkyl, and aryl;
R² is selected from hydrogen, substituted heteroaryl, and

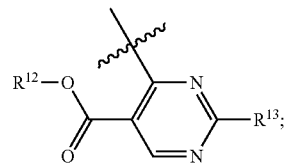

R³ is selected from hydrogen, NR⁵R⁶, OR⁷, SR⁷, and halogen;
R⁴ is selected from NR⁸R⁹ and OR¹⁰;
R⁵ and R⁶ are independently selected from hydrogen, alkyl, aryl, -alkyl-aryl, and —C(O)R¹¹;
R⁷ is selected from alkyl, aryl, and -alkyl-aryl;
R⁸ and R⁹ are independently selected from hydrogen, alkyl, aryl, and -alkyl-aryl;
R¹⁰ is selected from alkyl, aryl, and -alkyl-aryl;
in an alternative embodiment R¹⁰ is alkenyl;
R¹¹ is selected from alkyl and aryl;
R¹² is selected from alkyl, aryl, and -alkyl-aryl;
R¹³ is selected from —S-alkyl and Cl; and
each instance of R⁵⁰ is independently selected from hydrogen, halogen, and alkyl.

In one embodiment of the above invention y is 0 and n is 1 resulting in the synthetic method below:

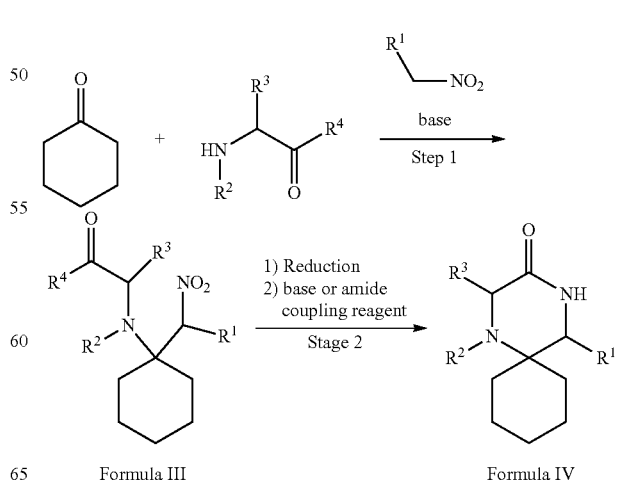

Formula III            Formula IV

Scheme 9. Additional preparation of compounds of Formula IV with only two isolation steps.

In another aspect of the invention a useful synthetic intermediate of Formula I is provided:

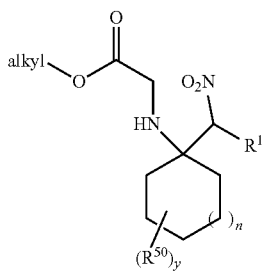

(I)

or an acceptable salt, N-oxide, or isotopic derivative thereof; wherein, y is 0, 1, 2, 3, or 4;

n is 0 or 1;

$R^1$ is selected from hydrogen, alkyl, and aryl; and each instance of $R^{50}$ is independently selected from hydrogen, halogen, and alkyl.

In one embodiment, the compound of Formula I is:

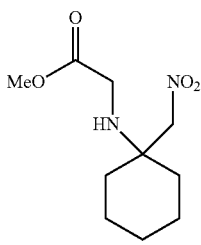 [SMILES: COC(=O)CNC1(C[N+](=O)[O-])CCCCC1]

or an acceptable salt, N-oxide, or isotopic derivative thereof.

In another aspect of the invention a useful synthetic intermediate of Formula III is provided:

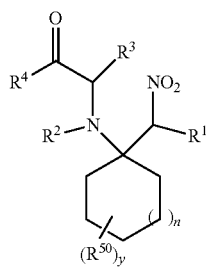

(III)

or an acceptable salt, N-oxide, or isotopic derivative thereof; wherein, y is 0, 1, 2, 3, or 4;

n is 0 or 1;

$R^1$ is selected from hydrogen, alkyl, and aryl;

$R^2$ is selected from hydrogen, substituted heteroaryl, and

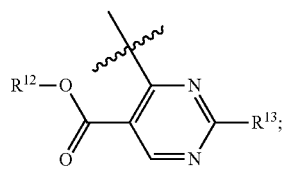

$R^3$ is selected from hydrogen, $NR^5R^6$, $OR^7$, $SR^7$, and halogen;

$R^4$ is selected from $NR^8R^9$ and $OR^{10}$;

$R^5$ and $R^6$ are independently selected from hydrogen, alkyl, aryl, -alkyl-aryl, and —C(O)$R^{11}$;

$R^7$ is selected from alkyl, aryl, and -alkyl-aryl;

$R^8$ and $R^9$ are independently selected from hydrogen, alkyl, aryl, and -alkyl-aryl;

$R^{10}$ is selected from alkyl, aryl, and -alkyl-aryl;

in an alternative embodiment $R^{10}$ is alkenyl;

$R^{11}$ is selected from alkyl and aryl;

$R^{12}$ is selected from alkyl, aryl, and -alkyl-aryl;

$R^{13}$ is selected from —S-alkyl and Cl; and each instance of $R^{50}$ is independently selected from hydrogen, halogen, and alkyl.

Non-limiting examples of embodiments of the present invention include the following:

Process A

Process A to prepare a spirocyclic compound of the present invention comprises the following steps: 1. reacting a cyclic ketone with a nitroalkane to afford a cycloalkyl group substituted with nitroalkylene; 2. reacting the compound of step (1) with a glycinate to afford a compound of Formula III; 3. reducing the compound of Formula III with a reducing agent; and 4. cyclizing the compound of step (3);

wherein the cyclic ketone is of Formula:

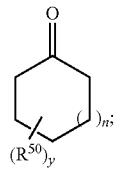

wherein the nitroalkane is of Formula:

wherein the glycinate is of Formula:

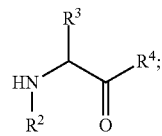

wherein Formula III is:

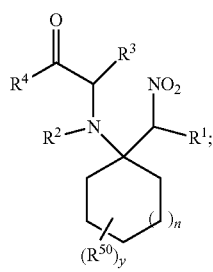

wherein the spirocyclic compound is of Formula:

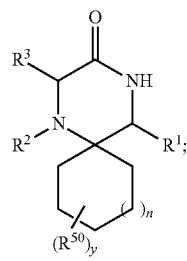

wherein
y is 0, 1, 2, 3, or 4;
n is 0 or 1;
$R^1$ is selected from hydrogen, alkyl, and aryl; and
$R^2$ is selected from hydrogen, substituted heteroaryl, and

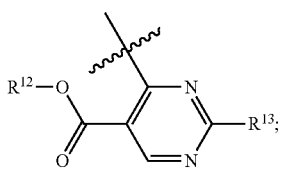

$R^3$ is selected from hydrogen, $NR^5R^6$, $OR^7$, $SR^7$, and halogen;
$R^4$ is selected from $NR^8R^9$ and $OR^{10}$;
$R^5$ and $R^6$ are independently selected from hydrogen, alkyl, aryl, -alkyl-aryl, and $-C(O)R^{11}$;
$R^7$ is selected from alkyl, aryl, and -alkyl-aryl;
$R^8$ and $R^9$ are independently selected from hydrogen, alkyl, aryl, and -alkyl-aryl;
$R^{10}$ is selected from alkyl, aryl, and -alkyl-aryl;
in an alternative embodiment $R^{10}$ is alkenyl;
$R^{11}$ is selected from alkyl and aryl;
$R^{12}$ is selected from alkyl, aryl, and -alkyl-aryl;
$R^{13}$ is selected from —S-alkyl and Cl; and
each instance of $R^{50}$ is independently selected from hydrogen, halogen, and alkyl.

Additional embodiments of Process A include the following:
(i) The process, wherein $R^1$ is hydrogen.
(ii) The process, wherein the nitroalkane is a solvent.
(iii) The process, wherein the nitroalkane is the only solvent.
(iv) The process, wherein an organic or inorganic base is used in step 1.
(v) The process, wherein a carbonate base is used in step 1.
(vi) The process, wherein potassium carbonate is used in step 1.
(vii) The process, wherein oxalic acid is added after step 2 to precipitate one or more undesired byproducts.
(viii) The process, wherein hydrobromic acid is added after step 2 to precipitate the compound of Formula III.
(ix) The process wherein alkyl is methyl.
(x) The process wherein alkyl is ethyl.
(xi) The process wherein alkyl is isopropyl.
(xii) The process wherein alkyl is tert-butyl.

Process B

Process B to prepare a spirocyclic compound of the present invention comprises the following steps: 1. reacting a cyclic ketone with a nitroalkane to afford a cycloalkyl group substituted with nitroalkylene; 2. reacting the compound of step (1) with an alkyl glycinate to afford a compound of Formula I; 3. reducing the compound of Formula I with a reducing agent; and 4. cyclizing the compound of step (3);

wherein the cyclic ketone is of Formula:

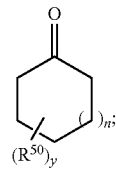

wherein the nitroalkane is of Formula:

wherein the alkyl glycinate is of Formula:

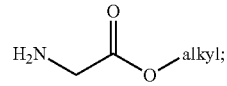

wherein Formula I is:

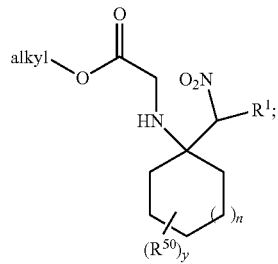

wherein the spirocyclic compound is of Formula:

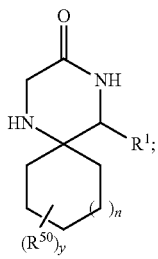

wherein
  y is 0, 1, 2, 3, or 4, and typically 0;
  n is 0 or 1;
  R¹ is selected from hydrogen, alkyl, and aryl; and
  each instance of R⁵⁰ is independently selected from hydrogen, halogen, and alkyl.

Additional embodiments of Process B include the following:
  (i) The process, wherein R¹ is hydrogen.
  (ii) The process, wherein the nitroalkane is a solvent.
  (iii) The process, wherein the nitroalkane is the only solvent.
  (iv) The process, wherein an organic or inorganic base is used in step 1.
  (v) The process, wherein a carbonate base is used in step 1.
  (vi) The process, wherein potassium carbonate is used in step 1.
  (vii) The process, wherein oxalic acid is added after step 2 to precipitate one or more undesired byproducts.
  (viii) The process, wherein hydrobromic acid is added after step 2 to precipitate the compound of Formula I.
  (ix) The process wherein alkyl is methyl.
  (x) The process wherein alkyl is ethyl.
  (xi) The process wherein alkyl is isopropyl.
  (xii) The process wherein alkyl is tert-butyl.

Process C

Process C to prepare a spirocyclic compound of the present invention comprises the following steps: 1. reducing a compound of Formula I with a reducing agent; and 2. cyclizing the compound of step (1);
  wherein Formula I is:

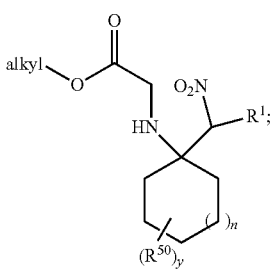

wherein the spirocyclic compound is of Formula:

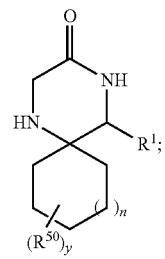

wherein
  y is 0, 1, 2, 3, or 4, and typically 0;
  n is 0 or 1;
  R¹ is selected from hydrogen, alkyl, and aryl; and
  each instance of R⁵⁰ is independently selected from hydrogen, halogen, and alkyl.

Additional embodiments of Process A, Process B, and Process C include the following:
  (i) The process, wherein the reducing agent is zinc.
  (ii) The process, wherein an acid is added in the reduction step.
  (iii) The process, wherein ammonium chloride is added in the reduction step.
  (iv) The process, wherein the reducing conditions comprise platinum (IV) oxide and hydrogen gas.
  (v) The process, wherein the reducing conditions comprise Raney nickel and hydrogen gas.
  (vi) The process, wherein the reducing agent is iron.
  (vii) The process, wherein the reducing agent is samarium diiodide.
  (viii) The process, wherein the reduction and cyclization occur in the same reaction vessel.
  (ix) The process, wherein water is a solvent used in the reduction step.
  (x) The process, wherein a mixture of water and acetone is used as the solvent in the reduction step.
  (xi) The process, wherein the reduction and cyclization are conducted at room temperature.
  (xii) The process, wherein the reduction and cyclization is conducted at about 15° C.
  (xiii) The process, wherein all of the steps are conducted at room temperature.
  (xiv) The process, wherein all of the steps are conducted at about 15° C.
  (xv) The process, wherein acid is added during the cyclization step.
  (xvi) The process, wherein base is added during the cyclization step.
  (xvii) The process, wherein neither acid nor base is added during the cyclization step.
  (xviii) The process wherein alkyl is methyl.
  (xix) The process wherein alkyl is ethyl.
  (xx) The process wherein alkyl is isopropyl.
  (xxi) The process wherein alkyl is tert-butyl.

Process D

Process D to prepare a compound of Formula I comprises the following steps: 1. reacting a cyclic ketone with a nitroalkane to afford a cycloalkyl group substituted with nitroalkylene; and 2. reacting the compound of step (1) with an alkyl glycinate;
  wherein the cyclic ketone is of Formula:

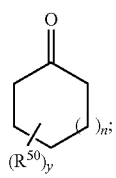

wherein the nitroalkane is of Formula:

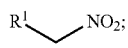

wherein the alkyl glycinate is of Formula:

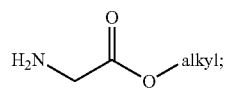

wherein Formula I is:

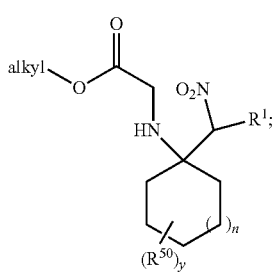

wherein
y is 0, 1, 2, 3, or 4, and typically 0;
n is 0 or 1;
$R^1$ is selected from hydrogen, alkyl, and aryl; and
each instance of $R^{50}$ is independently selected from hydrogen, halogen, and alkyl.

Additional embodiments of Process D include the following:
(i) The process, wherein $R^1$ is hydrogen.
(ii) The process, wherein the nitroalkane is a solvent.
(iii) The process, wherein the nitroalkane is the only solvent.
(iv) The process, wherein an organic or inorganic base is used in step 1.
(v) The process, wherein a carbonate base is used in step 1.
(vi) The process, wherein potassium carbonate is used in step 1.
(vii) The process, wherein oxalic acid is added after step 2 to precipitate one or more undesired byproducts.
(viii) The process, wherein hydrobromic acid is added after step 2 to precipitate the compound of Formula I.
(ix) The process wherein alkyl is methyl.
(x) The process wherein alkyl is ethyl.
(xi) The process wherein alkyl is isopropyl.
(xii) The process wherein alkyl is tert-butyl.

Process E

Process E to prepare a spirocyclic compound of the present invention comprises the following steps: 1. reacting a cyclic ketone with a nitroalkane to afford a cycloalkyl group substituted with nitroalkylene; 2. reacting the compound of step (1) with a protected glycinate to afford a compound of Formula I'; 3. reducing the compound of Formula I' with a reducing agent; and 4. cyclizing the compound of step (3);

wherein the cyclic ketone is of Formula:

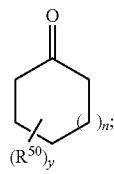

wherein the nitroalkane is of Formula:

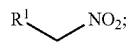

wherein the protected glycinate is of Formula:

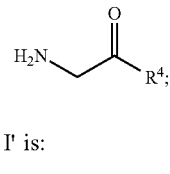

wherein Formula I' is:

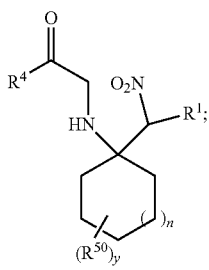

wherein the spirocyclic compound is of Formula:

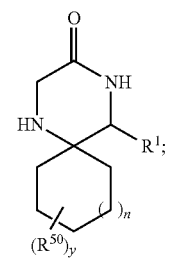

wherein
y is 0, 1, 2, 3, or 4, and typically 0;
n is 0 or 1;
$R^1$ is selected from hydrogen, alkyl, and aryl;
$R^4$ is selected from $NR^8R^9$ and $OR^{10}$;
$R^8$ and $R^9$ are independently selected from hydrogen, alkyl, aryl, cycloalkyl, and -alkyl-aryl;
$R^{10}$ is selected from alkyl, aryl, cycloalkyl, and -alkyl-aryl;

in an alternative embodiment $R^{10}$ is alkenyl; and each instance of $R^{50}$ is independently selected from hydrogen, halogen, and alkyl.

Additional embodiments of Process E include the following:

The process, wherein $R^1$ is hydrogen.

(ii) The process, wherein the nitroalkane is a solvent.

(iii) The process, wherein the nitroalkane is the only solvent.

(iv) The process, wherein an organic or inorganic base is used in step 1.

(v) The process, wherein a carbonate base is used in step 1.

(vi) The process, wherein potassium carbonate is used in step 1.

(vii) The process, wherein oxalic acid is added after step 2 to precipitate one or more undesired byproducts.

(viii) The process, wherein hydrobromic acid is added after step 2 to precipitate the compound of Formula I.

(ix) The process wherein $R^4$ is $OR^{10}$.

(x) The process wherein $R^4$ is $NR^8R^9$.

(xi) The process wherein $R^{10}$ is methyl.

(xii) The process wherein $R^{10}$ is ethyl.

(xiii) The process wherein $R^{10}$ is isopropyl.

(xiv) The process wherein $R^{10}$ is tert-butyl.

Process F

Process F to prepare a compound of Formula I' comprises the following steps: 1. reacting a cyclic ketone with a nitroalkane to afford a cycloalkyl group substituted with nitroalkylene; and 2. reacting the compound of step (1) with an alkyl glycinate;

wherein the cyclic ketone is of Formula:

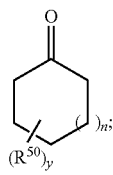

wherein the nitroalkane is of Formula:

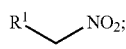

wherein the protected glycinate is of Formula:

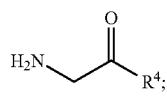

wherein Formula I' is:

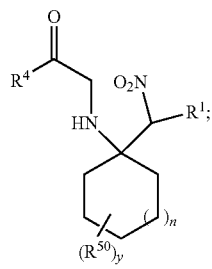

wherein y is 0, 1, 2, 3, or 4, and typically 0;

n is 0 or 1;

$R^1$ is selected from hydrogen, alkyl, and aryl;

$R^4$ is selected from $NR^8R^9$ and $OR^{10}$;

$R^8$ and $R^9$ are independently selected from hydrogen, alkyl, aryl, cycloalkyl, and -alkyl-aryl; and $R^{10}$ is selected from alkyl, aryl, cycloalkyl, and -alkyl-aryl;

in an alternative embodiment $R^{10}$ is alkenyl; and each instance of $R^{50}$ is independently selected from hydrogen, halogen, and alkyl.

Additional embodiments of Process F include the following:

(i) The process, wherein $R^1$ is hydrogen.

(ii) The process, wherein the nitroalkane is a solvent.

(iii) The process, wherein the nitroalkane is the only solvent.

(iv) The process, wherein an organic or inorganic base is used in step 1.

(v) The process, wherein a carbonate base is used in step 1.

(vi) The process, wherein potassium carbonate is used in step 1.

(vii) The process, wherein oxalic acid is added after step 2 to precipitate one or more undesired byproducts.

(viii) The process, wherein hydrobromic acid is added after step 2 to precipitate the compound of Formula I.

(ix) The process wherein alkyl is methyl.

(x) The process wherein alkyl is ethyl.

(xi) The process wherein alkyl is isopropyl.

(xii) The process wherein alkyl is tert-butyl.

In summary, the above processes use several innovations to achieve an improved yield and/or throughput. Non-limiting examples of these innovations include: (1) using nitromethane as the primary solvent and an inorganic base for the first step; (2) telescoping the Henry reaction to Michael addition which prevents formation of a structural isomer of the nitroolefin; (3) optionally using oxalic acid to remove excess methylglycinate from the first reaction mixture as the hemioxalate salt; and (4) optionally isolating the key nitro intermediate as the hydrobromide salt which stabilizes the intermediate and removes the need for further purification.

These advances have resulted in several advantages over previously reported routes, including: (1) the overall yield can now reach even up to about 50%, for example, up to about 20%, 30%, or 40%; (2) the number of isolated intermediates was reduced from 4-5 to 1; (3) the overall manufacturing time was significantly reduced; (4) there is less need for multiple steps (increased atom efficiency); and (5) several hazardous/difficult to handle reagents and the need for cryogenic cooling were eliminated.

BRIEF DESCRIPTION OF FIGURE

FIG. 1 is a flow diagram for the synthesis of 1,4-diazaspiro[5.5]undecan-3-one as described in Example 5. In one non-limiting illustrative example, the steps are as follows: 1) charge process water; 2) charge ammonium chloride; 3) charge acetone; 4) charge methyl (1-(nitromethyl)cyclohexyl)glycinate hydrobromide; 5) charge zinc powder in a portion-wise manner; 6) charge $K_2CO_3$ solution; 7) charge DCM; 8) charge composite organic layer; 9) charge cyclohexane. In one embodiment the reactor is degassed in between step 5 and step 6, then the mass is filtered after step 6, the aqueous layer from step 7 is discarded, the excess solvent from step 8 is distilled, and then the solid product is filtered after step 9. The boxes labeled 1 correspond to a single reactor being stirred for 1 hour. The boxes labeled 2 represent steps still occurring in the same reactor as 1 with the temperature maintained between 25° C. and 40° C. The box labeled 3 represents a step still occurring in the same reactor at a temperature between 25° C. and 40° C. with the reaction being stirred for 2 hours. The box labeled 4 represents the solid being removed by filtration and vacuum dried with heat.

DETAILED DESCRIPTION

I. Terminology

Compounds are described using standard nomenclature. Unless defined otherwise, all technical and scientific terms used herein have the same meaning as is commonly understood by one of skill in the art to which this invention belongs.

The compounds in any of the Formulas described herein include racemates, enantiomers, mixtures of enantiomers, diastereomers, mixtures of diastereomers, tautomers, N-oxides, isomers; such as rotamers, as if each is specifically described.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed. Unless defined otherwise, technical and scientific terms used herein have the same meaning as is commonly understood by one of skill in the art to which this invention belongs.

In an alternative embodiment of the present invention a compound of Formula I or Formula III is provided with at least one desired isotopic substitution of an atom, at an amount above the natural abundance of the isotope, i.e., enriched. Isotopes are atoms having the same atomic number but different mass numbers, i.e., the same number of protons but a different number of neutrons.

By way of general example and without limitation, isotopes of hydrogen, for example, deuterium ($^2H$) and tritium ($^3H$) may be used anywhere in described structures that achieves the desired result. Alternatively or in addition, isotopes of carbon, e.g., $^{13}C$ and $^{14}C$, may be used.

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one non-limiting embodiment, deuterium is 90, 95 or 99% enriched at a desired location.

In one non-limiting embodiment, the substitution of a hydrogen atom for a deuterium atom occurs within an R group selected from any of $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{50}$. For example, when any of the R groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, $OCDH_2$, $OCD_2H$, or $OCD_3$ etc.).

The compound of the present invention may form a solvate with solvents (including water). Therefore, in one non-limiting embodiment, the invention includes a solvated form of the compound. The term "solvate" refers to a molecular complex of a compound of the present invention (including a salt thereof) with one or more solvent molecules. Non-limiting examples of solvents are water, ethanol, dimethyl sulfoxide, acetone and other common organic solvents. The term "hydrate" refers to a molecular complex comprising a compound of the invention and water. Pharmaceutically acceptable solvates in accordance with the invention include those wherein the solvent may be isotopically substituted, e.g. $D_2O$, $d_6$-acetone, $d_6$-DMSO. A solvate can be in a liquid or solid form.

A dash ("-") that is not between two letters or symbols is used to indicate a point of attachment for a substituent. For example, —(C=O)NH$_2$ is attached through carbon of the keto (C=O) group.

"Alkyl" is a branched or straight chain saturated aliphatic hydrocarbon group. In one non-limiting embodiment, the alkyl group contains from 1 to about 12 carbon atoms, more generally from 1 to about 6 carbon atoms or from 1 to about 4 carbon atoms. In one non-limiting embodiment, the alkyl contains from 1 to about 8 carbon atoms. In certain embodiments, the alkyl is $C_1$-$C_2$, $C_1$-$C_3$, $C_1$-$C_4$, $C_1$-$C_5$, or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species. For example, the term $C_1$-$C_4$ alkyl as used herein indicates a straight or branched alkyl group having from 1, 2, 3, or 4 carbon atoms and is intended to mean that each of these is described as an independent species. Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, and 2,3-dimethylbutane. In an alternative embodiment, the alkyl group is optionally substituted. The term "Alkyl" also encompasses cycloalkyl or carbocyclic groups. For example, when a term is used that includes "alk" then "cycloalkyl" or "carbocyclic" can be considered part of the definition, unless unambiguously excluded by the context. For example, and without limitation, the terms alkyl, —O-alkyl, haloalkyl, etc. can all be considered to include the cyclic forms of alkyl, unless unambiguously excluded by context.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more cycloalkyl or heterocycle groups wherein the radical or point of attachment is on the aryl ring, and in such instances, the number of carbon atoms continue to designate the number of carbon atoms in the aryl ring system. The one or more fused cycloalkyl or heterocycle groups can be 4 to 7-membered saturated or partially unsaturated cycloalkyl or heterocycle groups.

The terms "heterocycle" include saturated, and partially saturated heteroatom-containing ring radicals, where the heteroatoms may be selected from nitrogen, sulfur, boron, silicone, and oxygen. Heterocyclic rings comprise monocyclic 3-10 membered rings, as well as 5-16 membered bicyclic ring systems (which can include bridged fused and spiro-fused bicyclic ring systems). It does not include rings containing —O—O—,—O—S— or —S—S— portions. Examples of saturated heterocycle groups include saturated 3- to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocycle radicals include but are not limited to, dihydrothienyl, dihydropyranyl, dihydrofuryl, and dihydrothiazolyl. Examples of partially saturated and saturated heterocycle groups include but are not limited to, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydroquinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl.

"Heterocycle" also includes groups wherein the heterocyclic radical is fused/condensed with an aryl or carbocycle radical, wherein the point of attachment is the heterocycle ring. For example, partially unsaturated condensed heterocyclic group containing 1 to 5 nitrogen atoms, for example, indoline, isoindoline, partially unsaturated condensed heterocyclic group containing 1 to 2 oxygen atoms and 1 to 3 nitrogen atoms, partially unsaturated condensed heterocyclic group containing 1 to 2 sulfur atoms and 1 to 3 nitrogen atoms, and saturated condensed heterocyclic group containing 1 to 2 oxygen or sulfur atoms.

The term "heteroaryl" denotes stable aromatic ring systems that contain one or more heteroatoms selected from O, N, and S, wherein the ring nitrogen and sulfur atom(s) are optionally oxidized, and nitrogen atom(s) are optionally quarternized. Examples include but are not limited to, unsaturated 5 to 6 membered heteromonocyclyl groups containing 1 to 4 nitrogen atoms, such as pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, IH-1,2,3-triazolyl, 2H-1,2,3-triazolyl]; unsaturated 5- to 6-membered heteromonocyclic groups containing an oxygen atom, for example, pyranyl, 2-furyl, 3-furyl, etc.; unsaturated 5 to 6-membered heteromonocyclic groups containing a sulfur atom, for example, 2-thienyl, 3-thienyl, etc.; unsaturated 5- to 6-membered heteromonocyclic groups containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic groups containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl]. In one embodiment the "heteroaryl" group is a 8, 9, or 10 membered bicyclic ring system. Examples of 8, 9, or 10 membered bicyclic heteroaryl groups include benzofurazanyl, benzothiophenyl, benzothiazolyl, benzoxazolyl, quinazolinyl, quinoxalinyl, naphthyridinyl, quinolinyl, isoquinolinyl, benzofuranyl, indolyl, indazolyl, and benzotriazolyl. As used herein "substituted heteroaryl" refers to a heteroaryl group that is substituted with the described substituents. If no substituents are explicitly described "substituted heteroaryl" refers to a heteroaryl group that is substituted with 1, 2, 3, or 4 substituents independently selected from F, Cl, Br, I, cyano, hydroxyl, —O-alkyl, —SH, —Salkyl, —COOH, —COOalkyl, —COalkyl, —COH, —CONH₂, —CONHalkyl, —CON(alkyl)₂, —OC(O)alkyl, —NHC(O)alkyl, —NalkylC(O)alkyl, nitro, amino, —NHalkyl, N(alkyl)₂, cyano, haloalkyl, aryl, heteroaryl, alkyl, alkenyl, alkynyl, haloalkyl, cycloalkyl, alkyl-aryl, alkyl-heteroaryl, alkyl-cycloalkyl, alkyl-heterocycle, heterocycle, —COOaryl, —COaryl, —CONHaryl, —CON(alkyl)(aryl), —OC(O)aryl, —NHC(O)aryl, —NalkylC(O)aryl, —COOheteroaryl, —COheteroaryl, —CONHheteroaryl, —CON(alkyl)(heteroaryl), —OC(O)heteroaryl, —NHC(O)heteroaryl, —NalkylC(O)heteroaryl, —COOheterocycle, —COheterocycle, —CONHheterocycle, —CON(alkyl)(heterocycle), —OC(O)heterocycle, —NHC(O)heterocycle, and -NalkylC(O)heterocycle.

As used herein, "carbocyclyl", "carbocyclic", "carbocycle" or "cycloalkyl" is a saturated or partially unsaturated (i.e., not aromatic) group containing all carbon ring atoms and from 3 to 14 ring carbon atoms ("$C_{3-14}$ cycloalkyl") and zero heteroatoms in the non-aromatic ring system. In some embodiments, a cycloalkyl group has 3 to 10 ring carbon atoms ("$C_{3-10}$ cycloalkyl"). In some embodiments, a cycloalkyl group has 3 to 9 ring carbon atoms ("$C_{3-9}$ cycloalkyl"). In some embodiments, a cycloalkyl group has 3 to 8 ring carbon atoms ("$C_{3-8}$ cycloalkyl"). In some embodiments, a cycloalkyl group has 3 to 7 ring carbon atoms ("$C_{3-7}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Exemplary $C_{3-6}$ cycloalkyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ cycloalkyl groups include, without limitation, the aforementioned $C_{3-6}$ cycloalkyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), and the like. Exemplary $C_{3-10}$ cycloalkyl groups include, without limitation, the aforementioned $C_{3-8}$ cycloalkyl groups as well as cyclononyl ($C_9$), cyclononenyl ($C_9$), cyclodecyl ($C_{10}$), cyclodecenyl ($C_{10}$), and the like. As the foregoing examples illustrate, in certain embodiments, the cycloalkyl group can be saturated or can contain one or more carbon-carbon double bonds.

II. Embodiments of the Present Invention

Embodiments of y and n

In one embodiment y is 0.
In one embodiment y is 1.
In one embodiment y is 2.
In one embodiment y is 3.
In one embodiment y is 4.
In one embodiment n is 0.
In one embodiment n is 1.
In one embodiment n is 0 and y is 0.
In one embodiment n is 0 and y is 1.
In one embodiment n is 0 and y is 2.
In one embodiment n is 0 and y is 3.
In one embodiment n is 0 and y is 4.
In one embodiment n is 1 and y is 0.
In one embodiment n is 1 and y is 1.
In one embodiment n is 1 and y is 2.
In one embodiment n is 1 and y is 3.
In one embodiment n is 1 and y is 4.
In one embodiment n is 1 and y is 5.

Embodiments of $R^1$

In one embodiment $R^1$ is hydrogen.
In one embodiment $R^1$ is alkyl.

Embodiments of $R^{50}$

In one embodiment at least one $R^{50}$ is halogen.
In one embodiment at least one $R^{50}$ is alkyl.
In one embodiment at least one $R^{50}$ is methyl.

Embodiments of "Alkyl"

In one embodiment "alkyl" is a $C_1$-$C_{10}$alkyl, $C_1$-$C_9$alkyl, $C_1$-$C_8$alkyl, $C_1$-$C_7$alkyl, $C_1$-$C_6$alkyl, $C_1$-$C_5$alkyl, $C_1$-$C_4$alkyl, $C_1$-$C_3$alkyl, or $C_1$-$C_2$alkyl.
In one embodiment "alkyl" has one carbon.
In one embodiment "alkyl" has two carbons.
In one embodiment "alkyl" has three carbons.
In one embodiment "alkyl" has four carbons.
In one embodiment "alkyl" has five carbons.
In one embodiment "alkyl" has six carbons.
Non-limiting examples of "alkyl" include: methyl, ethyl, propyl, butyl, pentyl, and hexyl.
Additional non-limiting examples of "alkyl" include: isopropyl, isobutyl, isopentyl, and isohexyl.
Additional non-limiting examples of "alkyl" include: sec-butyl, sec-pentyl, and sec-hexyl.
Additional non-limiting examples of "alkyl" include: tert-butyl, tert-pentyl, and tert-hexyl.
Additional non-limiting examples of "alkyl" include: neopentyl, 3-pentyl, and active pentyl.
In one embodiment "alkyl" is "substituted alkyl"
In one embodiment "alkenyl" is "substituted alkenyl"

In one embodiment "alkynyl" is "substituted alkynyl"

Embodiments of Formula III and Formula IV a. In one embodiment n is 0.
b. In another embodiment n is 1.
c. Embodiment a or b, wherein $R^1$ is hydrogen.
d. Embodiment a or b, wherein $R^1$ is alkyl.
e. Embodiment a or b, wherein $R^1$ is methyl.
f. Embodiment a or b, wherein $R^1$ is ethyl.
g. Embodiment a or b, wherein $R^1$ is propyl.
h. Embodiment a or b, wherein $R^1$ is cyclopropyl.
i. Any one of embodiments a-h, wherein $R^2$ is hydrogen.
j. Any one of embodiments a-h, wherein $R^2$ is substituted heteroaryl.
k. Any one of embodiments a-h, wherein $R^2$ is

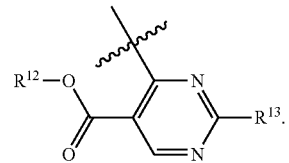

l. Embodiment k, wherein $R^{12}$ is alkyl.
m. Embodiment k, wherein $R^{12}$ is methyl.
n. Embodiment k, wherein $R^{12}$ is aryl.
o. Embodiment k, wherein $R^{12}$ is -alkyl-aryl.
p. Any one of embodiments k-o, wherein $R^{13}$ is —S-alkyl.
q. Any one of embodiments k-o, wherein $R^{13}$ is —S-methyl.
r. Any one of embodiments k-o, wherein $R^{13}$ is Cl.
s. Any one of embodiments a-r, wherein $R^3$ is hydrogen.
t. Any one of embodiments a-r, wherein $R^3$ is halogen.
u. Any one of embodiments a-r, wherein $R^3$ is $NR^5R^6$.
v. Embodiment u, wherein $R^5$ is hydrogen.
w. Embodiment u, wherein $R^5$ is alkyl.
x. Embodiment u, wherein $R^5$ is —C(O)$R^{11}$.
y. Embodiment x, wherein $R^{11}$ is alkyl.
z. Embodiment x, wherein $R^{11}$ is aryl.
aa. Any one of embodiments u-z, wherein $R^6$ is hydrogen.
bb. Any one of embodiments u-z, wherein $R^6$ is alkyl.
cc. Any one of embodiments a-r, wherein $R^3$ is $OR^7$.
dd. Any one of embodiments a-r, wherein $R^3$ is $SR^7$.
ee. Embodiment cc or dd, wherein $R^7$ is alkyl, aryl, and -alkyl-aryl.
ff. Embodiment cc or dd, wherein $R^7$ is aryl.
gg. Embodiment cc or dd, wherein $R^7$ is -alkyl-aryl.
hh. Any one of embodiments a-gg, wherein $R^4$ is $NR^8R^9$.
ii. Embodiment hh, wherein $R^8$ is hydrogen.
jj. Embodiment hh, wherein $R^8$ is alkyl.
kk. Embodiment hh, wherein $R^8$ is alkyl-aryl.
ll. Any one of embodiments hh-kk, wherein $R^9$ is hydrogen.
mm. Any one of embodiments hh-kk, wherein $R^9$ is alkyl.
nn. Any one of embodiments hh-kk, wherein $R^9$ is alkyl-aryl.
oo. Any one of embodiments a-gg, wherein $R^4$ is $OR^{10}$.
pp. Embodiment oo, wherein $R^{10}$ is alkyl.
qq. Embodiment oo, wherein $R^{10}$ is aryl.
rr. Embodiment oo, wherein $R^{10}$ is -alkyl-aryl.
ss. Any one of embodiments a-rr, wherein at least one $R^{50}$ is alkyl.
tt. Any one of embodiments a-rr, wherein at least one $R^{50}$ is halogen.

uu. Any one of embodiments a-rr, wherein y is 0.
vv. Any one of embodiments a-uu, wherein y is 1.
ww. Any one of embodiments a-uu, wherein y is 2.
xx. Any one of embodiments a-uu, wherein y is 3.
yy. Any one of embodiments a-uu, wherein y is 4.
zz. Any one of embodiments a-zz, wherein alkyl is methyl.
aaa. Any one of embodiments a-zz, wherein alkyl is ethyl.
bbb. Any one of embodiments a-zz, wherein alkyl-aryl is benzyl.

Additional Embodiments of $R^2$

In certain embodiments "substituted heteroaryl" is a 6-membered heteroaryl group substituted with 1, 2, 3, or 4 substituents independently selected from halogen, C(O)OH, C(O)Oalkyl, C(O)NH$_2$, C(O)NHalkyl, C(O)Nalkyl$_2$, —S-alkyl, —S(O)-alkyl, and —S(O)$_2$alkyl.

In certain embodiments $R^2$ is

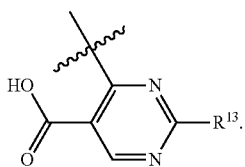

In certain embodiments $R^2$ is

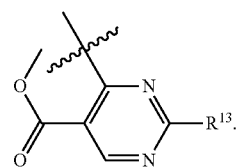

In certain embodiments $R^2$ is

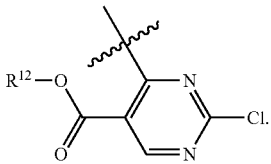

In certain embodiments $R^2$ is

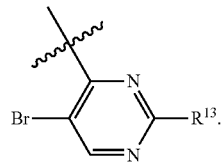

In certain embodiments $R^2$ is

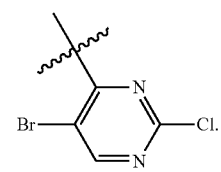

In certain embodiments $R^2$ is

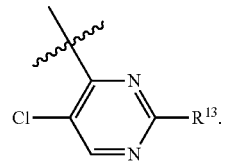

In certain embodiments $R^2$ is

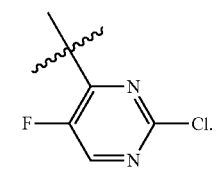

In certain embodiments $R^2$ is

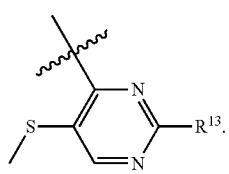

In certain embodiments $R^2$ is

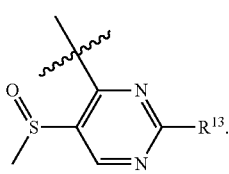

In certain embodiments $R^2$ is

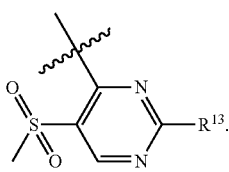

III. Synthesis of Compounds of Formula I and Formula III

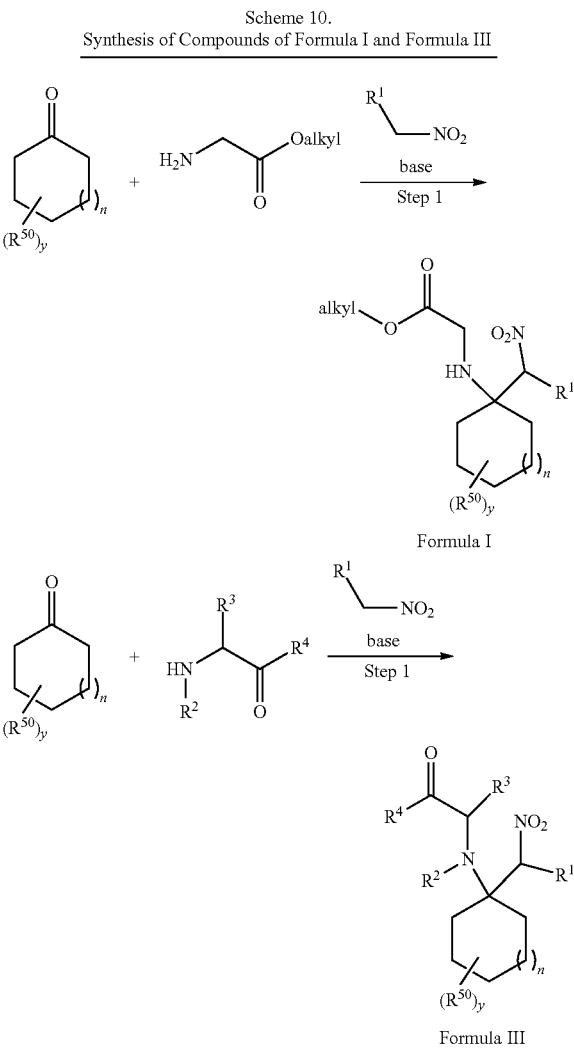

Scheme 10.
Synthesis of Compounds of Formula I and Formula III

It has been discovered that compounds of Formula I and Formula III, such as methyl (1-(nitromethyl)cyclohexyl) glycinate and analogues thereof, are advantageously prepared by conducting a Henry reaction followed by elimination and Michael addition. Using this sequence prepares new glycinates and allows for the synthesis of 1,4-diazaspiro[5.5] undecan-3-one with superior yield and throughput. These mechanistic steps can be advantageously conducted in one pot to afford compounds of Formula I and Formula III in one synthetic step.

This synthetic sequence starting from a cyclohexanone and undergoing nucleophilic addition (Henry reaction) followed by elimination of water, nucleophilic conjugate addition of an alkyl glycinate (Michael addition) is shown above in Scheme 10.

Step 1

Generally, Step 1 can be accomplished in a polar aprotic solvent at room temperature in the presence of a base that facilitates the reaction. Any polar aprotic solvent can be used that achieves the desired result. In one embodiment nitromethane or substituted nitromethane is used as both a reactant and the solvent. The order of addition may be varied in a manner that achieves a suitable result. The order in which cyclic ketone, glycinate, and potassium carbonate is added to nitromethane or substituted nitromethane often does not significantly affect the yield. The order of addition of glycinate and cyclic ketone can be modified, if desired and favorable. In certain embodiments a solvent used is methyl-t-butyl ether. In certain embodiments a solvent used is cyclohexane.

In one embodiment, the concentration of cyclohexanone is at least about 0.5 M, 0.6 M, 0.7 M, 0.8 M, 0.9 M, 1M, 1.25M, 1.5M, 1.75 M, or 2 M.

In another embodiment, the cyclic ketone is substituted cyclohexanone, substituted cyclopentanone, unsubstituted cyclohexanone, or unsubstituted cyclopentanone.

In another embodiment, the glycinate is methyl glycinate, ethyl glycinate, isopropyl glycinate or tert-butyl glycinate. For example, the glycinate may be methyl glycinate.

Any suitable base can be used in Step 1 that achieves the desired result. In one embodiment, the base is an inorganic base selected from potassium carbonate, calcium carbonate, magnesium carbonate, sodium carbonate, cesium carbonate, sodium bicarbonate, potassium bicarbonate, magnesium bicarbonate, calcium bicarbonate, lithium hydroxide, sodium hydroxide, potassium hydroxide, magnesium hydroxide, calcium hydroxide, strontium hydroxide, and barium hydroxide.

In another embodiment the base is an organic base selected from DIPEA (N,N-diisopropylethylamine), DMAP (4-dimethylaminopyridine), DBU (1,8 diazabicycloundec-7-ene), TEA (triethylamine), pyridine, trimethylamine, tripropylamine, triisopropylamine, dimethylaniline, dimethylbenzylamine, DABCO (1,4-diazabicyclo[2.2.2]octane), 1,5-diazabicyclo[4.3.0]non-5-ene, 2,6-lutidine, morpholine, piperidine, piperazine, proton-sponge, and 1,5,7-triazabicyclo[4.4.0]dec-5-ene.

The selected glycinate in a typical embodiment is more nucleophilic than the base used. In one embodiment the glycinate is in the form of a salt, for example a hydrochloride salt.

The temperature can be any temperature that provides the desired yield, in the desired time, with minimal undesired byproducts. In non-limiting embodiments, the temperature may be from about 0° C. to about 50° C., from about 10° C. to about 50° C., from about 10° C. to about 40° C., from about 20° C. to about 40° C., or from about 20° C. to about 30° C. In one non-limiting embodiment, the temperature is selected to be room temperature. In another non-limiting embodiment, the temperature is from about 25° C. to about 35° C.

The reaction can be allowed to proceed for a sufficient time to obtain the desired yield of product. In non-limiting embodiments, the reaction may proceed in Step 1 for about 0.5 hours to about 10 hours, for about 0.5 hours to about 8 hours, for about 1 hour to about 8 hours, for about 1 hour to about 6 hours, for about 1 hour to about 4 hours, or for about 1 hour to about 3 hours. It should be understood by those of skill in the art that the time and temperature of the reaction are related. For example, if a higher temperature is suitable and doesn't result in an unacceptable level of side products, then a lower reaction time may obtain the desired yield. Alternatively, a lower temperature may require a higher reaction time with fewer side products.

The reaction can be allowed to proceed for a sufficient time to obtain the desired yield of product. In non-limiting embodiments, the reaction may proceed in Step 1 in less than 14 hours, less than 10 hours, less than 6 hours, less than 4 hours, or less than 3 hours.

The reaction can be allowed to proceed for a sufficient time to obtain the desired yield of product. In non-limiting embodiments, the reaction may proceed in Step 1 for about 5 hours to about 24 hours, for about 6 hours to about 22 hours, for about 7 hours to about 20 hours, for about 8 hours to about 19 hours, for about 9 hours to about 18 hours, for about 10 hours to about 17 hours, for about 11 hours to about 16 hours, for about 12 hours to about 16 hours, or for about 13 hours to about 15 hours.

In one embodiment the compound of Formula I or Formula III may be isolated in the form of a salt. In one example, hydrobromic acid or a similar acid can be added at the end of the reaction to collect the compound of Formula I or Formula III as a solid. In another embodiment, oxalic acid or a similar organic acid is added to chemically remove any remaining glycinate starting material as a solid. These two acidic isolation steps can be used together, for example after workup the oxalic acid can be added and the excess glycinate starting material removed by filtration. After removal of the excess glycinate, hydrobromic acid can be added to the mixture to precipitate the pure compound of Formula I or Formula III as a hydrobromide salt.

In some non-limiting examples, the glycinate is used in excess to the cyclic ketone. At least about 1.2, 1.5, 1.7, 2, 2.2, 2.5, 2.7, or 3 equivalents of glycinate may be used in this embodiment. In another embodiment the cyclic ketone is used in excess to the glycinate. At least about 1.2, 1.5, 1.7, 2, 2.2, 2.5, 2.7, or 3 equivalents of cyclic ketone may be used in this embodiment. In the above embodiments any equivalents of base is used that afford the product in the desired yield and purity. In one embodiment at least about 1, 1.2, 1.5, 1.7, 2, 2.2, 2.5, 2.7, 3, 3.2, 3.5, 3.7, or 4 equivalents of base are used.

The reaction can be allowed to proceed for a sufficient time to obtain the desired yield of product. For example, in one embodiment, the reaction is allowed to proceed for up to about 15 minutes, 30 minutes, 45 minutes, 1 hour, 2 hours, 3 hours, 4 hours, 6 hours, or 10 hours. It should be understood by those of skill in the art that the time and temperature of the reaction are related. For example, if a higher temperature is suitable and doesn't result in an unacceptable level of side products, then a lower reaction time may obtain the desired yield. Alternatively, a lower temperature may require a higher reaction time with fewer side products.

In one embodiment the conditions described herein are used to synthesis methyl (1-(nitromethyl)cyclohexyl)glycinate.

IV. Synthesis of Compounds of Formula II and Formula IV

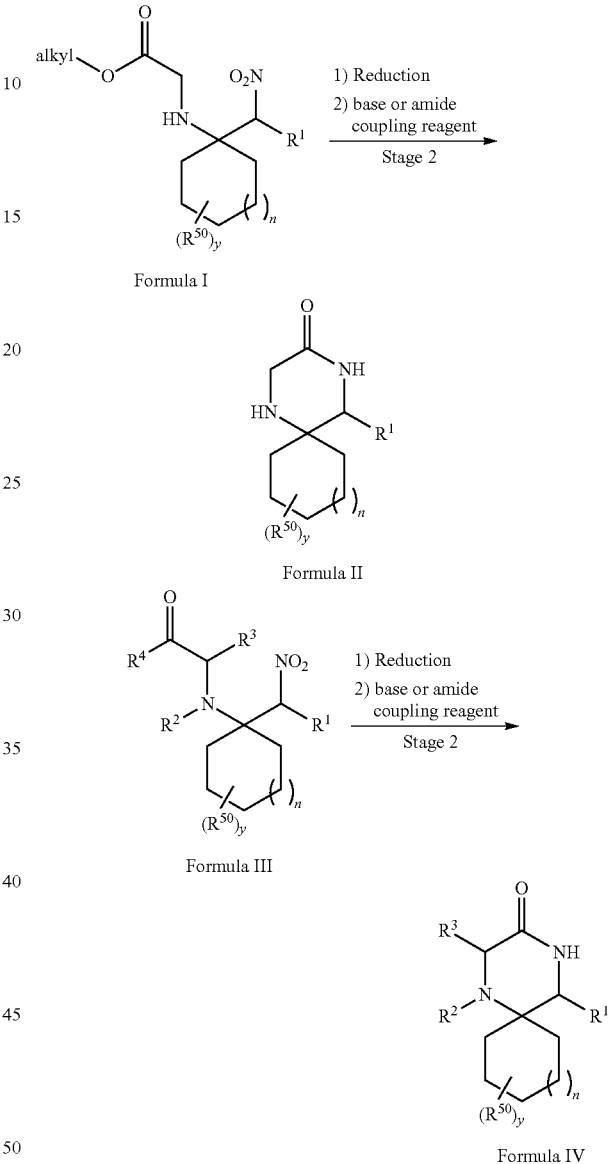

It has been discovered that compounds of Formula II and Formula IV, such as 1,4-diazaspiro[5.5]undecan-3-one and analogues thereof, are advantageously prepared from compounds of Formula I or Formula III or their pharmaceutically acceptable salts. The compound of Formula I or Formula III or its salt can be prepared as described above.

Advantages of this method include high yields, less need for protection and deprotection, increased atom efficiency, fewer hazardous reagents, fewer steps, and shorter manufacturing time.

This synthetic sequence starting from a compound of Formula II or Formula IV and undergoing reduction, hydrolysis, and cyclization is shown below in Scheme 11. In one embodiment cyclization and hydrolysis occur at the same time.

Stage 2

Generally, Stage 2 can be accomplished in a solvent or mixture of solvents that facilitates the reaction. The reagents can be added with a variation in order to achieve a suitable result. In one embodiment the reduction agent is compatible with the base or amide coupling reagent and thus all the reactants and reagents are added at the beginning of the reaction. In this embodiment the entire process starting from a cyclic ketone is two synthetic steps with multiple transformations. In another embodiment the reduction reagent is added first followed by addition of the base or amide coupling reagent after the desired period of time has passed.

In one embodiment the intramolecular cyclization proceeds without addition of a base or amide coupling reagent. For example, the intramolecular cyclization can proceed after reduction of the nitro group to an amine with no additional reagents being necessary.

In certain embodiments, methyl-t-butyl ether is used as a solvent. In certain embodiments cyclohexane is used as a solvent.

In one aspect the initial concentration of the compound of Formula I or Formula III is at least about 0.5 M, 0.6 M, 0.7 M, 0.8 M, 0.9 M, 1 M, 1.25 M, 1.5 M, 1.75 M, or 2 M. The reducing reagents and conditions used in Step 1 can be any which achieve the desired goal. In one aspect, the reductant is zinc activated with a weak acid such as ammonium chloride or acetic acid. In another embodiment the reductant is platinum(IV) oxide in the presence of hydrogen gas, Raney nickel in the presence of hydrogen gas, iron, or samarium diiodide. In certain embodiments the reducing agent is zinc dust.

In one embodiment, at least about 10, 8, 6, 5, 4, 3, or 2 equivalents of reductant are used. For example, at least about 10, 8, 6, 5, 4, 3, or 2 equivalents of Zinc are used. The skilled artisan will recognize that different equivalencies of reductant will affect the rate of reduction. For example, the reductant may stall at 2 equivalents of Zinc but proceed without issue at 5 equivalents of zinc.

In certain examples, the base can be an inorganic base selected from potassium carbonate, calcium carbonate, magnesium carbonate, sodium carbonate, cesium carbonate, sodium bicarbonate, potassium bicarbonate, magnesium bicarbonate, calcium bicarbonate, lithium hydroxide, sodium hydroxide, potassium hydroxide, magnesium hydroxide, calcium hydroxide, strontium hydroxide, and barium hydroxide.

In another embodiment, the base is an organic base selected from DIPEA (N,N-diisopropylethylamine), DMAP (4-dimethylaminopyridine), DBU (1,8 diazabicycloundec-7-ene), TEA (triethylamine), pyridine, trimethylamine, tripropylamine, triisopropylamine, dimethylaniline, dimethylbenzylamine, DABCO (1,4-diazabicyclo[2.2.2]octane), 1,5-diazabicyclo[4.3.0]non-5-ene, 2,6-lutidine, morpholine, piperidine, piperazine, proton-sponge, and 1,5,7-triazabicyclo[4.4.0]dec-5-ene.

The temperature can be any temperature that provides the desired yield, in the desired time, with minimal undesired byproducts. For example, the temperature may be from about 0° C. to about 50° C., from about 10° C. to about 50° C., from about 10° C. to about 40° C., from about 20° C. to about 40° C., or from about 20° C. to about 30° C. In one non-limiting embodiment, the temperature is selected to be room temperature.

The reaction can be allowed to proceed for a sufficient time to obtain the desired yield of product. For example, in one embodiment, the reaction is allowed to proceed for up to about 5 minutes, 10 minutes, 15 minutes, 30 minutes, 45 minutes, 1 hour, 2 hours, 3 hours, or 4 hours. It should be understood by those of skill in the art that the time and temperature of the reaction are related. For example, if a higher temperature is suitable and doesn't result in an unacceptable level of side products, then a lower reaction time may obtain the desired yield. Alternatively, a lower temperature may require a higher reaction time with fewer side products.

In one embodiment the conditions described herein are used to synthesis 1,4-diazaspiro[5.5]undecan-3-one from methyl (1-(nitromethyl)cyclohexyl)glycinate.

V. Compounds of the Present Invention

Non-limiting examples of compounds of the present invention include:

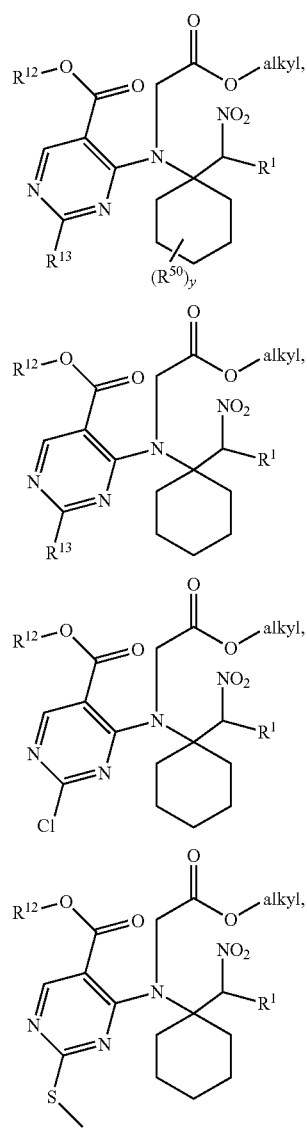

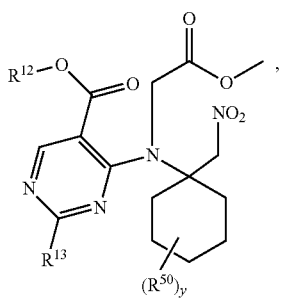
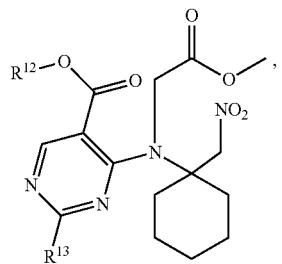
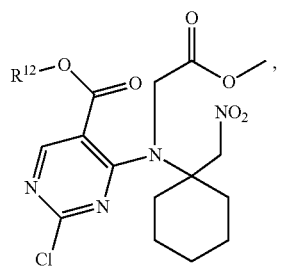
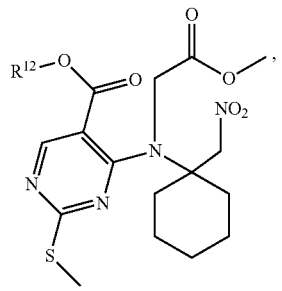
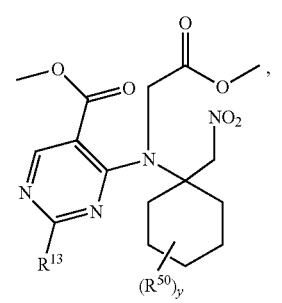
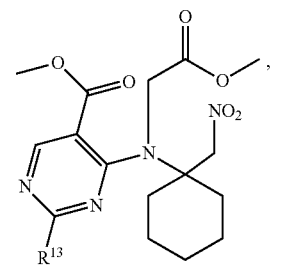
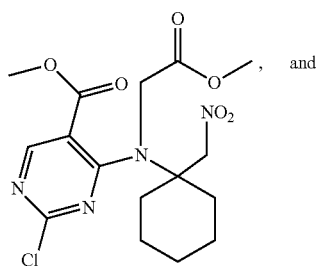
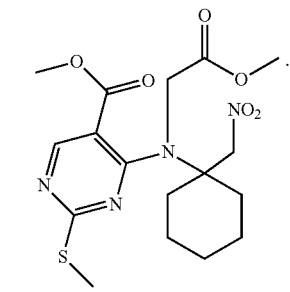
Additional non-limiting examples of compounds of the present invention include:
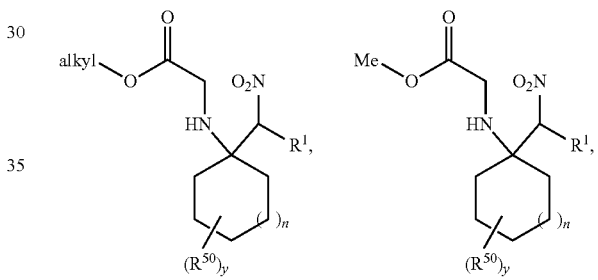
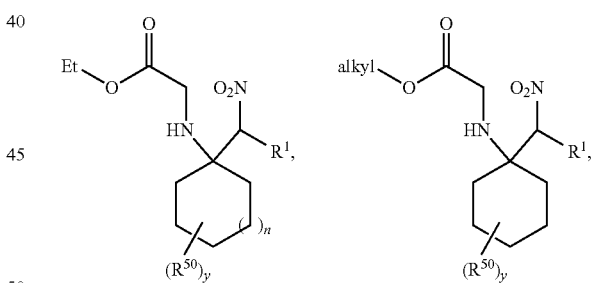
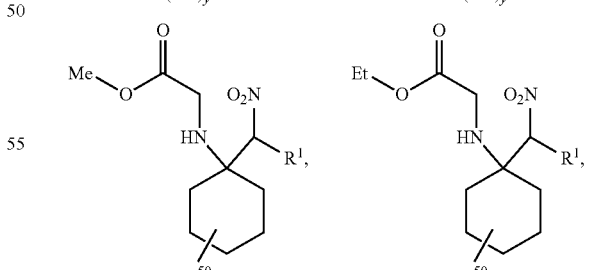

-continued
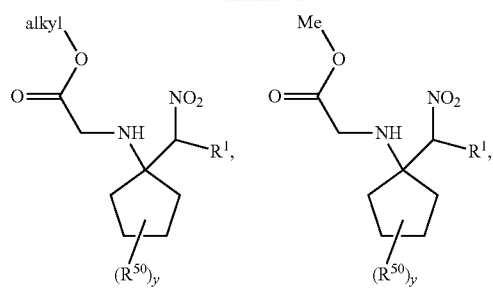
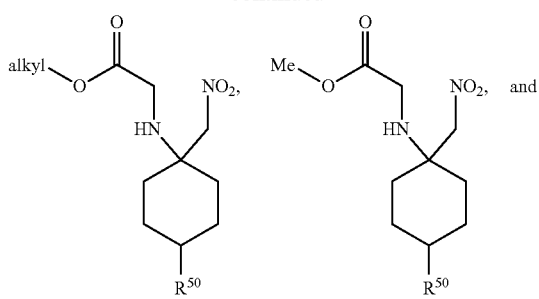
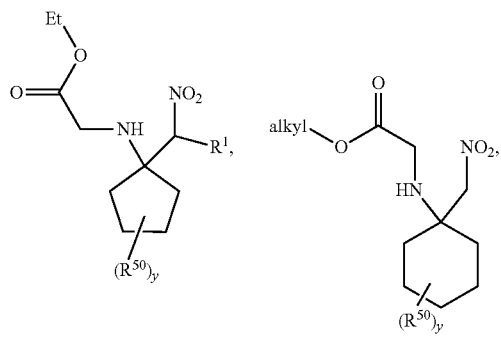
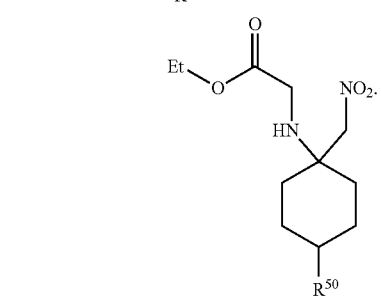
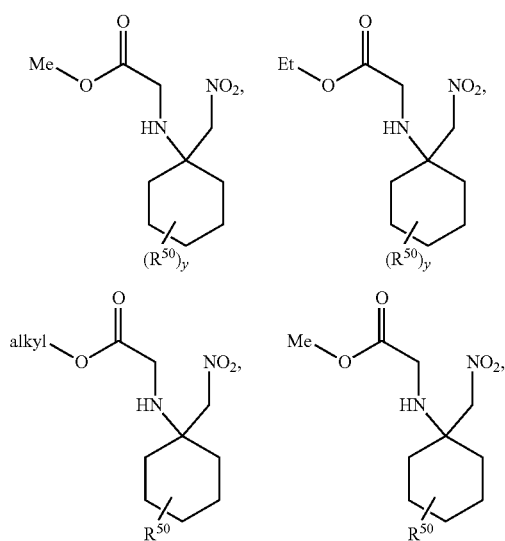
Additional non-limiting examples of compounds of the present invention include:
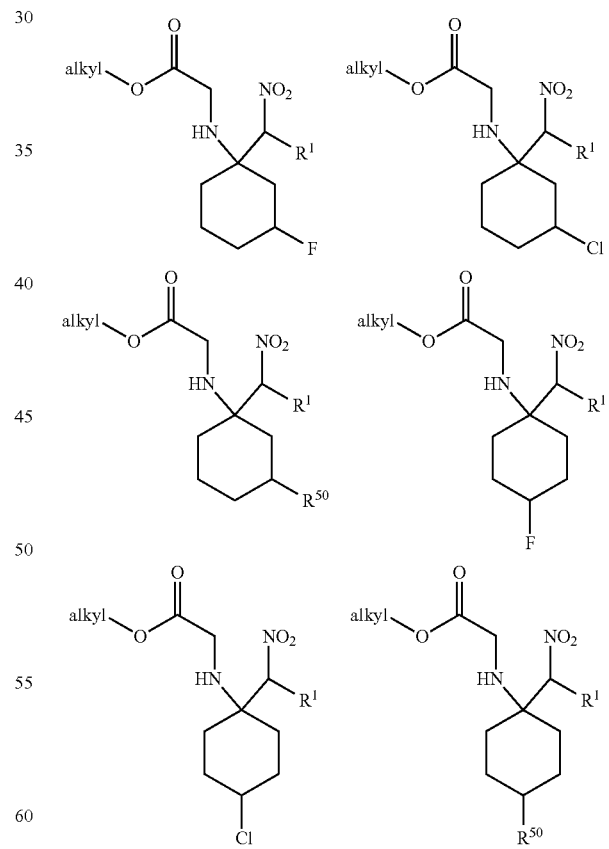
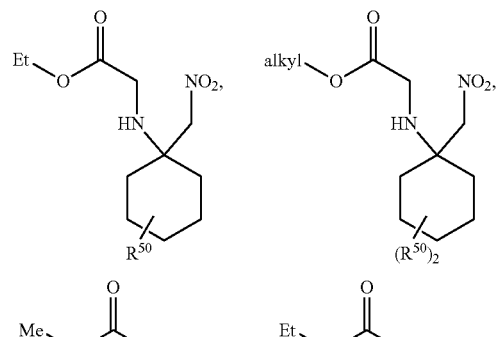
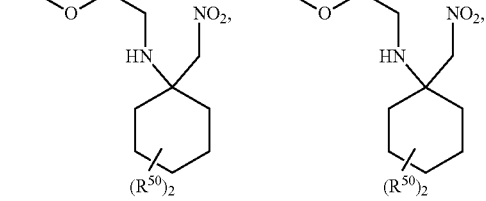

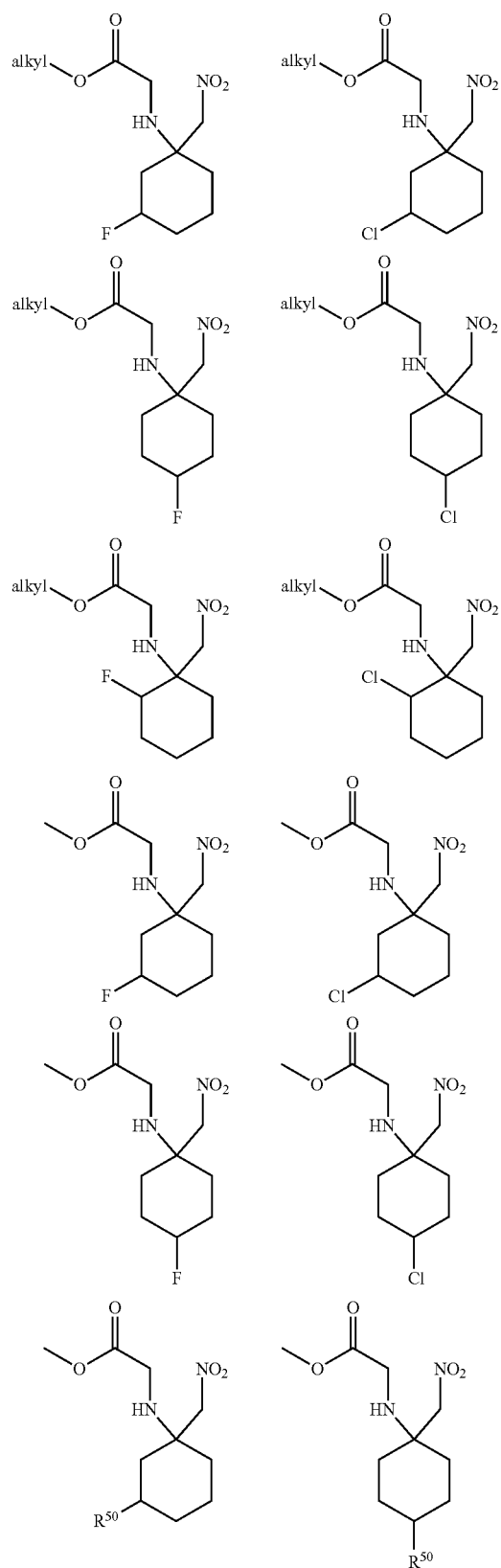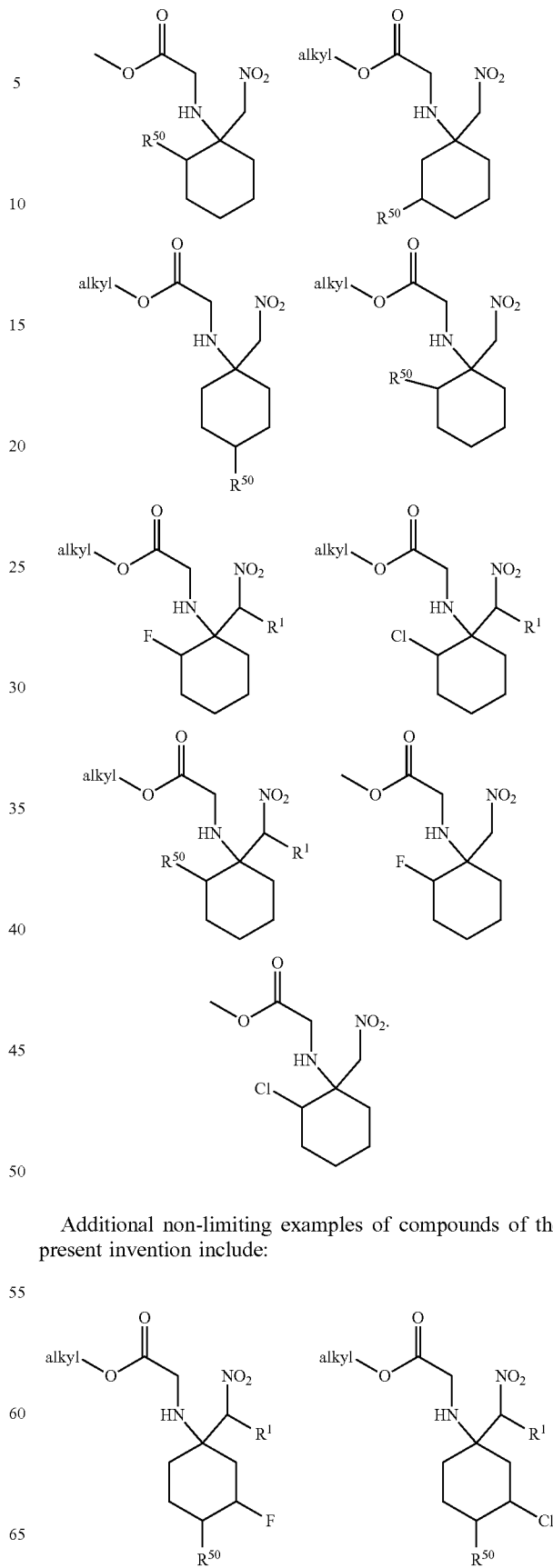
Additional non-limiting examples of compounds of the present invention include:
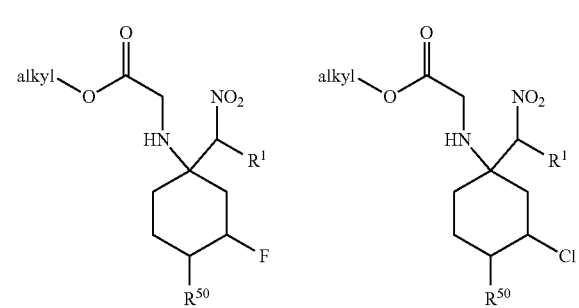

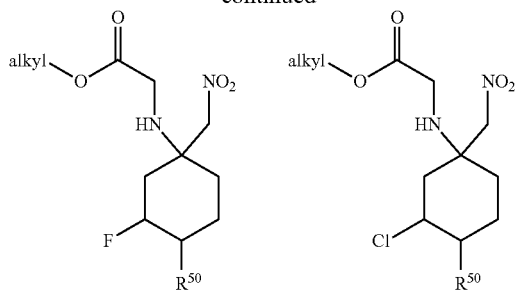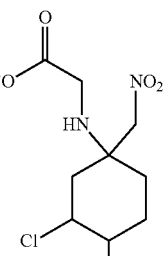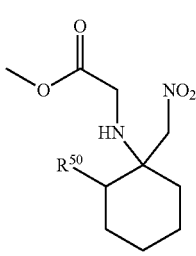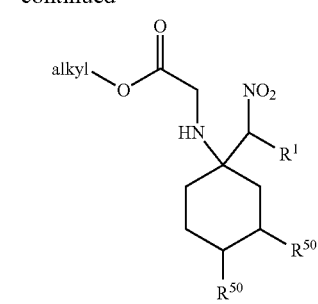
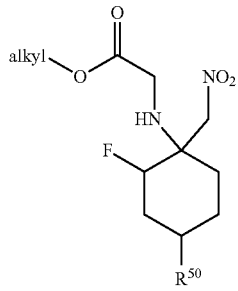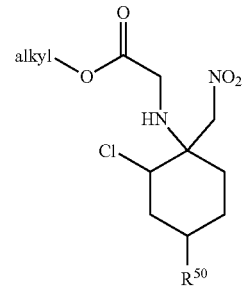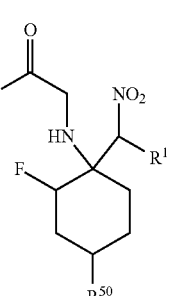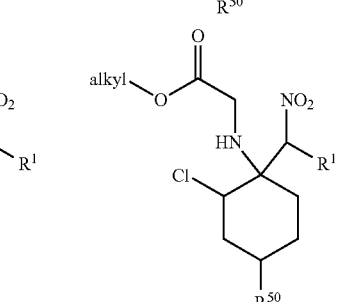
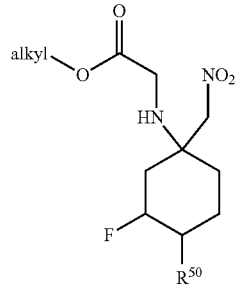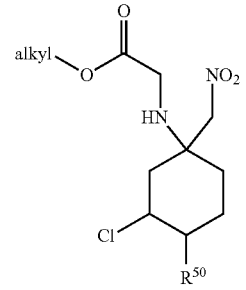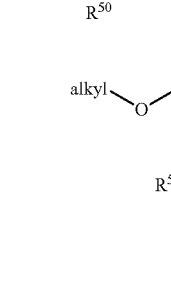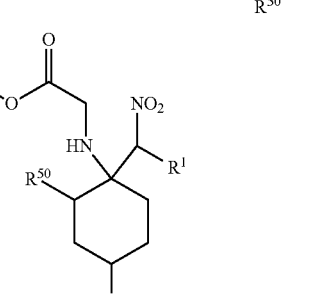
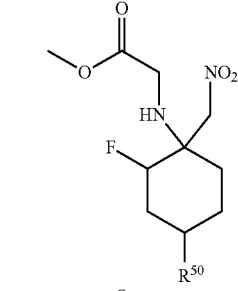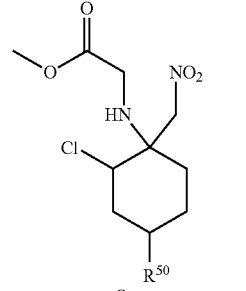
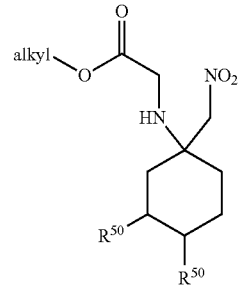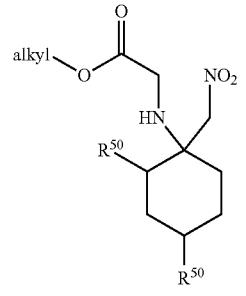
Non-limiting examples of compounds that can be synthesized according to the methods of the present invention include:
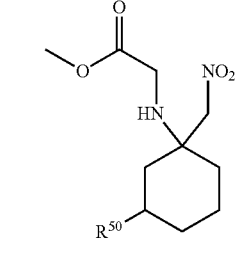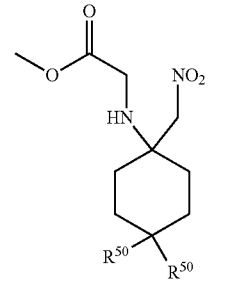
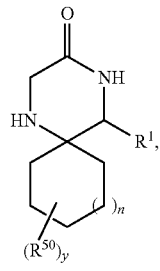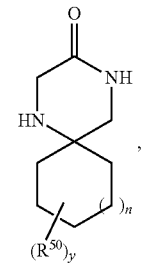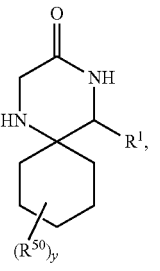
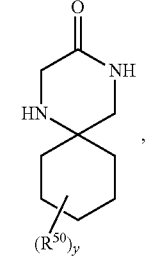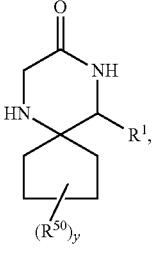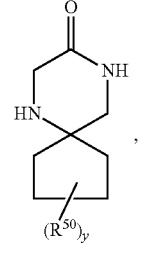

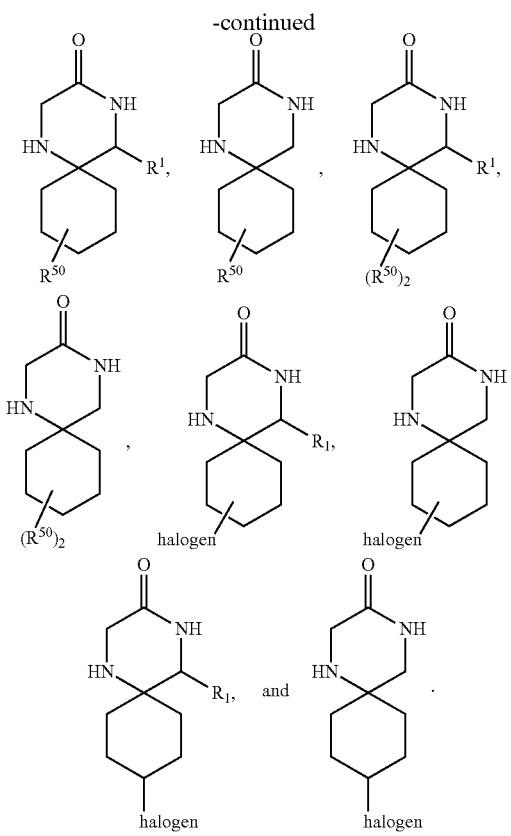

Additional non-limiting examples of compounds that can be synthesized according to the methods of the present invention include:

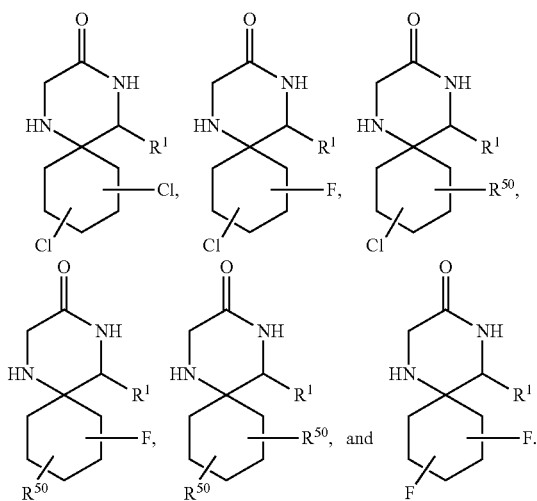

VI. Illustrative Examples

General Methods

The structure of starting materials, intermediates, and final products was confirmed by standard analytical techniques, such as, for example, NMR spectroscopy and/or mass spectrometry. Unless otherwise noted, reagents and solvents were used as received from commercial suppliers. Proton nuclear magnetic resonance spectra were obtained on a 300 MHz in Chloroform-d. HPLC analyses were performed on a Waters SunFire C18, 150×4.6 mm, 4.6 μm column.

Example 1. Synthesis of Methyl (1-(nitromethyl)cyclohexyl)glycinate Hydrobromide

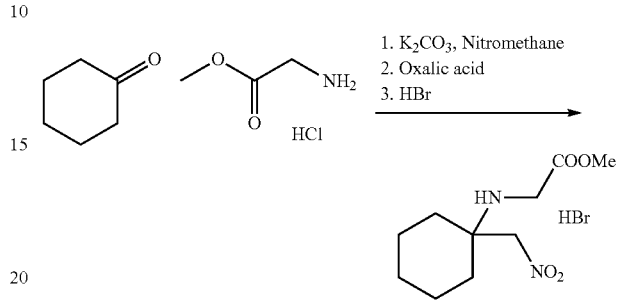

A suspension of cyclohexanone (4 g, 40.8 mmol), methyl glycinate hydrochloride (12.79 g, 102 mmol, 2.5 eq.) and potassium carbonate (14.08 g, 102 mmol, 2.5 eq.) in nitromethane (50 ml) was stirred at room temperature for 2 hours. The reaction mixture was then diluted with dichloromethane and filtered through a fritted funnel. The residue was washed several times with dichloromethane. The combined filtrates were concentrated to dryness and the remaining oil was dissolved in ether. A solution of oxalic acid (1.835 g, 20.38 mmol, 0.5 eq.) in 5 mL methanol was added under stirring, concentrated to dryness, re-suspended in ether and sonicated for 10 min. The solid was filtered off, washed with ether and air dried. Analysis of this solid confirmed that it was methyl glycinate hemioxalate (5.5 g). To the filtrate was added hydrogen bromide (7.14 ml, 40.8 mmol, 33% in Acetic Acid, 1 eq.) under stirring. The suspension was stirred for 10 min., sonicated for 10 min and the solids were isolated by filtration, washed with ether and air dried to give methyl (1-(nitromethyl)cyclohexyl)glycinate, HBr (11.4 g, 36.6 mmol, 91% yield) as an off-white solid.

$^1$H NMR (300 MHz, Chloroform-d) δ 1.52 (q, J=15.2, 14.1 Hz, 2H), 1.79 (d, J=13.6 Hz, 6H), 1.98 (d, J=13.1 Hz, 2H), 3.85 (s, 3H), 4.23 (s, 2H), 5.13 (s, 2H).

Example 2. Alternative synthesis of Methyl (1-(nitromethyl)cyclohexyl)glycinate Hydrobromide

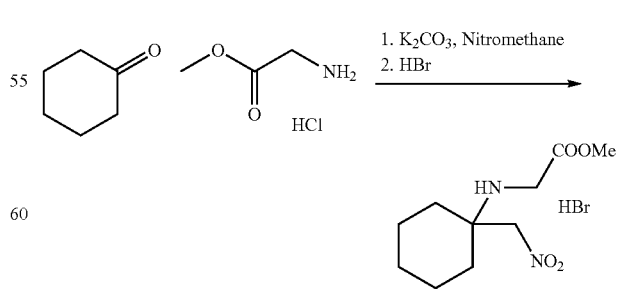

A suspension of cyclohexanone (4 g, 40.8 mmol), methyl glycinate hydrochloride (12.79 g, 102 mmol, 2.5 eq.) and potassium carbonate (14.08 g, 102 mmol, 2.5 eq.) in nitromethane (50 ml) is stirred at room temperature for 2 hours. The reaction mixture is then diluted with dichloromethane and filtered through a fritted funnel. The residue is washed several times with dichloromethane. The combined filtrates are concentrated to dryness and the remaining oil is dissolved in ether. To the solution of hydrogen bromide (7.14 ml, 40.8 mmol, 33% in acetic acid, 1 eq.) is added under stirring. The suspension is stirred for 10 min., sonicated for 10 min and the solids are isolated by filtration, washed with ether and air dried to give methyl (1-(nitromethyl)cyclohexyl)glycinate, HBr salt.

Alternatively, the above method may be used to prepare methyl (1-(nitromethyl)cyclohexyl)glycinate as a free base by using an alternative method of purification instead of using hydrogen bromide.

Example 3. Synthesis of
1,4-Diazaspiro[5.5]undecan-3-one

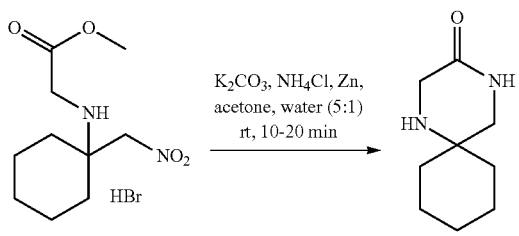 [SMILES: COC(=O)CNC1(C[N+](=O)[O-])CCCCC1 ; Br ; O=C1CNC2(CCCCC2)CN1]

To a suspension of methyl (1-(nitromethyl)cyclohexyl) glycinate hydrobromide (2 g, 6.43 mmol) in acetone (30 ml) and water (6.00 ml) was added ammonium chloride (3.44 g, 64.3 mmol, 10 eq.), potassium carbonate (0.888 g, 6.43 mmol, 1 eq.) and zinc (4.2 g, 64.3 mmol, 10 eq.) and the mixture was stirred vigorously for 10 min. The volatiles were removed under vacuum and the residue was treated with a saturated solution of $K_2CO_3$. The mixture was filtered through a fritted funnel and the residue was washed several times with water and ethyl acetate. The layers were separated, and the aqueous layer was extracted with ethyl acetate (three times). The combined organic layers were dried over sodium sulfate, filtered and concentrated under reduced pressure to provide a crude mixture, which was triturated with isopropyl ether. The solids were isolated by filtration and air-dried to give 1,4-diazaspiro[5.5]undecan-3-one (674 mg, 4.01 mmol, 62.3% yield) as an off-white solid.

$^1$H NMR (300 MHz, Chloroform-d) δ 1.41-1.62 (m, 10H); 3.16, 3.17 (d, J=2.6 Hz, 2H), 3.48 (s, 2H), 6.22 (s, 1H).

Example 4. Alternative Synthesis of Methyl
(1-(nitromethyl)cyclohexyl)glycinate Hydrobromide

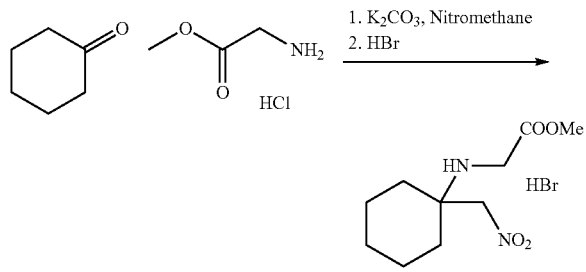

Nitrogen was applied to a reactor vessel followed by vacuum to not less than 450 mm Hg. Nitrogen was applied once again and then the reactor was rinsed with nitromethane. The reactor was charged with nitromethane (4 L) followed by potassium carbonate (2.5 kg) and methylglycinate (3.2 kg). A solution of cyclohexanone (1 kg) in nitromethane (3.5 L) was prepared and added to the reaction. All steps were completed at approximately 25° C.

The reaction mass was cooled to 10° C. and process water (2.5 L) was added in a dropwise manner for not less than 180 minutes. The water addition was conducted at 10° C. The temperature was then raised to 30° C. and the reaction was stirred at 30° C. for 14 hours or until the cyclohexanone content was not more than 5% by TLC. The reaction mixture was next diluted with 2M potassium carbonate (10 L) at 30° C. and the reaction mass was stirred at 30° C. for 5 minutes before methyl-t-butyl ether (10 L) was added and the reaction was stirred for an additional 40 minutes at 30° C.

The organic layer was separated from the aqueous layer and the aqueous layer was mixed with methyl-t-butyl ether (10 L) and allowed to stir for 30 minutes at 30° C. The process was repeated twice. The aqueous layers were discarded. The three organic layers were combined and methyl-t-butyl ether (20 L) was added to further dilute the reaction mixture. The solution was cooled to 5° C. and hydrogen bromide solution (1.9 L, 33% in acetic acid) was added for not less than 240 minutes. The mixture was then stirred at 5° C. for 3 hours. The reaction mass was then filtered and washed with methyl-t-butyl ether (0.5 L). The mass was dried at 25° C. until the mother liquor was completely removed and the wet cake was further dried in a vacuum over at 50° C. for 4-5 hours.

Example 5. Alternative Synthesis of
1,4-Diazaspiro[5.5]undecan-3-one

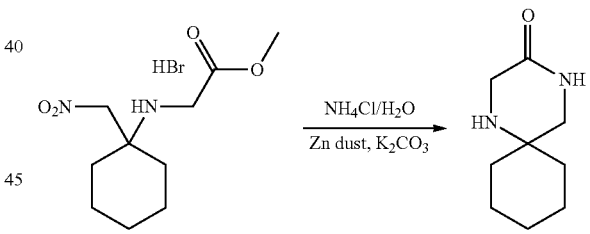

A reactor was charged with process water (1.9 L) followed by ammonium chloride (0.60 kg) and then acetone (7.5 kg). The reaction was stirred for 10 minutes. Methyl (1-(nitromethyl)cyclohexyl)glycinate hydrobromide (1 kg) was added to the reactor followed by zinc powder (0.75 kg) portion wise for 30 minutes. The reaction was stirred for 30 minutes at 50° C. or until the methyl (1-(nitromethyl) cyclohexyl)glycinate hydrobromide content was not more than 0.5%.

The acetone was completely distilled out under vacuum at 55° C. and the pH of the resulting solution was adjusted to pH 10-11 using 2M potassium carbonate. The solution was stirred at 25° C. for 30 minutes. The reaction was then filtered through a pad of celite and the resulting reaction mass was charged with 10% MeOH in DCM (10 kg) and stirred for 30 minutes to separate the organics from the aqueous materials. This was repeated 6 times. The resulting aqueous layers were discarded. The organic layers were concentrated to dryness and triturated with cyclohexane (055 kg). The solution was stirred for 20 minutes at 5° C., filtered, and washed with cyclohexane (0.20 kg). The wet material was then dried in a vacuum oven at 55° C. to afford 0.18 kg of product. (In an alternative embodiment, the trituration is conducted with methyl-t-butyl ether.

This specification has been described with reference to embodiments of the invention. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

We claim:

1. A process to prepare a spirocyclic compound comprising:
   a. reacting a cyclic ketone with a nitroalkane to afford a cycloalkyl group substituted with nitroalkylene;
   b. reacting the compound of step (a) with a glycinate to afford a compound of Formula III;
   c. reducing the compound of Formula III with a reducing agent;
   d. cyclizing the compound of step (c);
   wherein the cyclic ketone is of Formula:

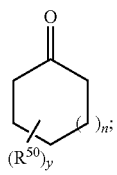

wherein the nitroalkane is of Formula:

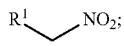

wherein the glycinate is of Formula:

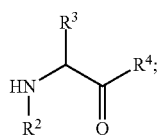

wherein Formula III is:

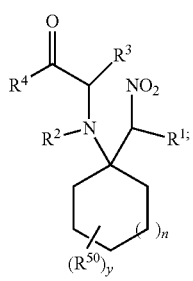

wherein the spirocyclic compound is of Formula:

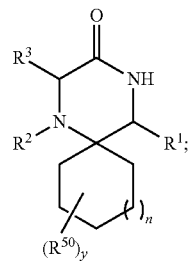

wherein y is 0;

n is 0 or 1;

$R^1$ is hydrogen;

$R^2$ is hydrogen, substituted heteroaryl, or

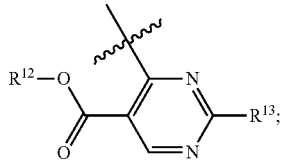

$R^3$ is hydrogen;

$R^4$ is $NR^8R^9$ or $OR^{10}$;

$R^5$ and $R^6$ are independently selected from the group consisting of hydrogen, alkyl, aryl, -alkyl-aryl, and —C(O)$R^{11}$;

$R^7$ is alkyl, aryl, or -alkyl-aryl;

$R^8$ and $R^9$ are independently selected from the group consisting of hydrogen, alkyl, aryl, and -alkyl-aryl;

$R^{10}$ is alkyl, aryl, or -alkyl-aryl;

$R^{11}$ is alkyl or aryl;

$R^{12}$ is alkyl, aryl, or -alkyl-aryl;

$R^{13}$ is —S-alkyl or Cl.

2. The process of claim 1, wherein the nitroalkane is also a solvent.

3. The process of claim 1, wherein a base is used in step (a).

4. The process of claim 3, wherein the base is an organic base.

5. The process of claim 3, wherein the base is an inorganic base.

6. The process of claim 1, wherein oxalic acid is added after step (b) to precipitate and remove byproducts.

7. The process of claim 1, wherein an acid is added after step (b) to isolate the compound of Formula I as a salt.

8. The process of claim 7, wherein the acid is hydrobromic acid.

9. The process of claim 1, wherein n is 1.

10. The process of claim 1, wherein $R^4$ is —OMe or —OEt.

11. The process of claim 1, wherein the spirocyclic compound is:

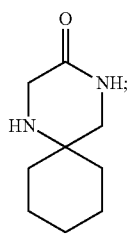

and wherein the compound of Formula III is:

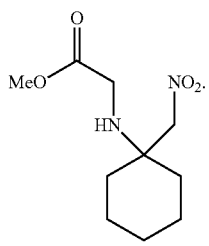 [SMILES: COC(=O)CNC1(C[N+](=O)[O-])CCCCC1]

12. A compound of Formula

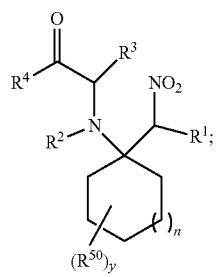

or an acceptable salt thereof;
wherein
y is 0, 1, 2, 3, or 4;
n is 0 or 1;
$R^1$ is hydrogen, alkyl, or aryl;
$R^2$ is hydrogen, substituted heteroaryl, or

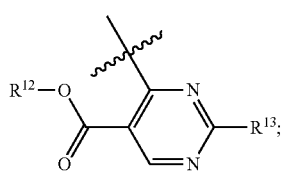

$R^3$ is hydrogen, $NR^5R^6$, $OR^7$, $SR^7$, or halogen;
$R^4$ is $NR^8R^9$ or $OR^{10}$;
$R^5$ and $R^6$ are independently selected from the group consisting of hydrogen, alkyl, aryl, -alkyl-aryl, and —C(O)$R^{11}$;
$R^7$ is alkyl, aryl, or -alkyl-aryl;
$R^8$ and $R^9$ are independently selected from the group consisting of hydrogen, alkyl, aryl, and -alkyl-aryl;
$R^{10}$ is alkyl, aryl, or -alkyl-aryl;
$R^{11}$ is alkyl or aryl;
$R^{12}$ is alkyl, aryl, or -alkyl-aryl; and
$R^{13}$ is —S-alkyl or Cl;

each instance of $R^{50}$ is independently selected from the group consisting of hydrogen, halogen, and alkyl.

13. The compound of claim 12, wherein y is 1.
14. The compound of claim 13, wherein $R^{50}$ is halogen.
15. The compound of claim 13, wherein $R^{50}$ is alkyl.
16. The compound of claim 12, wherein $R^1$ is hydrogen.
17. The compound of claim 16, wherein n is 1.
18. The compound of claim 17, wherein y is 0.
19. The compound of claim 18, wherein $R^2$ is hydrogen.
20. The compound of claim 19, wherein $R^3$ is hydrogen.
21. The compound of claim 20, wherein $R^4$ is —OMe or —OEt.
22. The compound of claim 12, wherein the compound is of Formula:

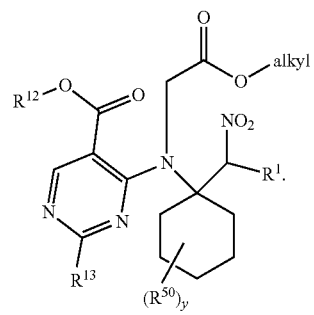

23. The compound of claim 12, wherein the compound is of Formula:

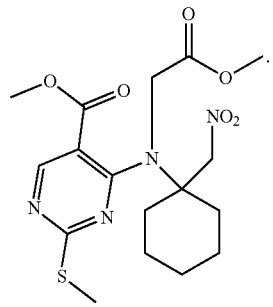

24. The compound of claim 12, wherein the compound is of structure:

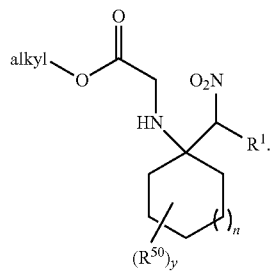

25. The compound of claim 12, wherein the compound is of structure:

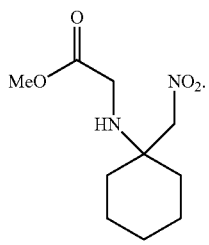 [SMILES: COC(=O)CNC1(C[N+](=O)[O-])CCCCC1]

26. A process to prepare a compound of Formula III comprising:
   a. reacting a cyclic ketone with a nitroalkane to afford a cycloalkyl group substituted with nitroalkylene;
   b. reacting the compound of step (a) with a glycinate;
   wherein the cyclic ketone is of Formula:

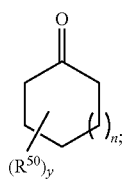

wherein the nitroalkane is of Formula:

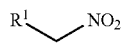

wherein the glycinate is of Formula:

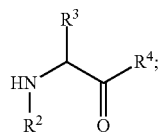

wherein Formula III is:

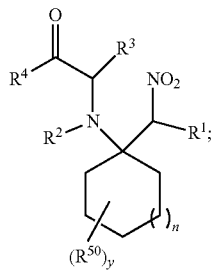

wherein
y is 0;
n is 0 or 1;
$R^1$ is hydrogen;
$R^2$ is hydrogen, substituted heteroaryl, or

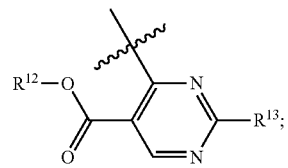

$R^3$ is hydrogen;
$R^4$ is $NR^8R^9$ or $OR^{10}$;
$R^5$ and $R^6$ are independently selected from the group consisting of hydrogen, alkyl, aryl, -alkyl-aryl, and —C(O)$R^{11}$;
$R^7$ is alkyl, aryl, or -alkyl-aryl;
$R^8$ and $R^9$ are independently selected from the group consisting of hydrogen, alkyl, aryl, and -alkyl-aryl;
$R^{10}$ is alkyl, aryl, or -alkyl-aryl;
$R^{11}$ is alkyl or aryl;
$R^{12}$ is alkyl, aryl, or -alkyl-aryl;
$R^{13}$ is —S-alkyl or Cl.

\* \* \* \* \*